(12) United States Patent
Takai et al.

(10) Patent No.: US 7,310,139 B2
(45) Date of Patent: Dec. 18, 2007

(54) EVALUATION METHOD AND DEVICE FOR GEL STATE OR SOL-GEL STATE CHANGE OF OBJECT

(75) Inventors: Touichirou Takai, Nonoichi-machi (JP); Misao Tomita, Nonoichi-machi (JP); Hideaki Kawahara, Nonoichi-machi (JP); Tooru Awazu, Nonoichi-machi (JP); Makoto Diou, Nonoichi-machi (JP); Taku Kitaura, Nonoichi-machi (JP); Kazuo Hosotani, Nonoichi-machi (JP); Ikuo Togashi, Nonoichi-machi (JP); Masato Nishi, Nonoichi-machi (JP); Motonari Amano, Nonoichi-machi (JP); Takahiro Matsuura, Nonoichi-machi (JP)

(73) Assignees: Takai Tofu & Soymilk Equipment Company Limited, Ishikawa-Gun (JP); Matsuuradenkosha Company Limited, Ishikawa-ku (JP)

( * ) Notice: Subject to any disclaimer, the term of this patent is extended or adjusted under 35 U.S.C. 154(b) by 185 days.

(21) Appl. No.: 10/508,902
(22) PCT Filed: Mar. 28, 2003
(86) PCT No.: PCT/JP03/04021

§ 371 (c)(1),
(2), (4) Date: Sep. 23, 2004

(87) PCT Pub. No.: WO03/087790

PCT Pub. Date: Oct. 23, 2003

(65) Prior Publication Data
US 2005/0225752 A1    Oct. 13, 2005

(30) Foreign Application Priority Data
Mar. 28, 2002  (JP) .............................. 2002-092979

(51) Int. Cl.
*G01N 21/00* (2006.01)
(52) U.S. Cl. .................................. 356/237.1
(58) Field of Classification Search ............. 356/237.1, 356/446, 511–512
See application file for complete search history.

(56) References Cited

U.S. PATENT DOCUMENTS 4,641,527 A * 2/1987 Hiroi et al. ................... 73/582

(Continued)

FOREIGN PATENT DOCUMENTS

JP    7-301602    11/1995

(Continued)

OTHER PUBLICATIONS

K. Hara, et al., "2D Optical Characterzation of the Gelation Process of Tungstic Acid", Reports on Progress in Polymer Physics in Japan, XXXV, 1992, pp. 477 to 480.

(Continued)

*Primary Examiner*—Gregory J. Toatley, Jr.
*Assistant Examiner*—Juan D. Valentin, II
(74) *Attorney, Agent, or Firm*—Greenblum & Bernstein, P.L.C.

(57) ABSTRACT

A system and method for evaluating a material body by a scattered light observation system which observes a gel state or a gel-formable sol state material body illuminated with a coherent light through a two dimensional image recognizing means, including measuring a gel state or a change in sol-gel state of said material body using a light section formed on an image forming surface or conditions of a speckle pattern.

18 Claims, 16 Drawing Sheets

U.S. PATENT DOCUMENTS 6,417,916 B1 * 7/2002 Dengler et al. ............ 356/35.5

FOREIGN PATENT DOCUMENTS

| JP | 10-120795 | 5/1998 |
| JP | 10-339694 | 12/1998 |
| JP | 11-60249 | 3/1999 |
| JP | 2000-149087 | 5/2000 |
| JP | 2000-214086 | 8/2000 |
| JP | 2003-106995 | 4/2003 |
| WO | WO 88/07179 | 9/1988 |

OTHER PUBLICATIONS

K. Hara, et al., "Evolution of the 2-Dimensional Intensity Distribution of the Scattered Lights from Gelling Tungstic Acid", Jpn. J. Appl. Phys., vol. 32, No. 2, 1993, pp. 996-1000.

Solid State Physics, vol. 28, No. 4, 1993.

Homepage of Otsuka Denshi, rietieved on Mar. 16, 2002.

T. Dor, et al., "The Continuous Observation of Milk Coagulation with Light Scattering by Means of Optical Fiber", Journal of Food Science and Technology, Col. 39, No. 4, 1992, pp. 309-315.

* cited by examiner

RELATIONSHIP BETWEEN HARDNESS OF GELATIN GEL AND SPECKLE VALUE

- ● PACK SURFACE
- ○ PACK REAR FACE
- — LINEARLY (PACK SURFACE)
- – – LINEARLY (PACK REAR FACE)

RELATIONSHIP BETWEEN HARDNESS OF AGAR GEL
AND SPECKLE VALUE

- ● PACK SURFACE
- ○ PACK REAR FACE
- − − LOGARITHM APPROXIMATE CURVE (PACK REAR SURFACE)
- —— LOGARITHM APPROXIMATE CURVE (PACK SURFACE)

RELATIONSHIP BETWEEN HARDNESS OF COFFEE-CONTAINING CARRAGEENAN AND SPECKLE VALUE

- PACK REAR FACE
— POWER APPROXIMATE CURVE

RELATIONSHIP BETWEEN HARDNESS OF ALBUMEN GEL AND SPECKLE VALUE

● PACK REAR FACE
— LOGARITHM APPROXIMATE CURVE

RELATIONSHIP BETWEEN HARDNESS OF PACKED TOFU AND SPECKLE VALUE

○ SPECKLE VALUE
— POWER APPROXIMATE CURVE

SPECKLE VALUE AND FRACTURE FORCE UNDER
PACKAGED STATE (HOT PACKED TOFU)

● PACKAGED STATE
○ UNSEALED STATE
— MULTINOMIAL (PACKAGED STATE)
-- MULTINOMIAL (UNSEALED STATE)

COAGULATION STEP OF SOYBEAN MILK BY
VARIOUS COAGULANTS

—×— NO ADDITION
—■— GDL
—▲— CLEAR POWDER
—●— LIQUID BITTERN
—○— EMULSION BITTERN
—△— TRANSGLUTAMINASE

INFLUENCE OF EXCITATION IN MEASUREMENT OF PACKED TOFU

— ● — COMPLETELY STATIC CONDITION
— ○ — AT EXCITATION

EVALUATION METHOD AND DEVICE FOR GEL STATE OR SOL-GEL STATE CHANGE OF OBJECT

TECHNICAL FIELD

This invention relates to a method and a device for the non-destructive, non-contact and quick evaluation of changes in the gel state and sol-gel state of a material body capable of causing changes in the gel state and sol-gel state of a gel material body, using a two dimensional image-analyzing technique and making use of an image formation or speckle pattern of a coherent irradiation light section as the index.

BACKGROUND OF THE INVENTION

Several methods are known for carrying out observation of gelation process or gel state based on the two dimensional light scattering intensity. For example, there are a method for observing gelation process and state of a non-ergodicity sample (JP-A-2000-214086), a method for measuring gelation degree of polyvinyl chloride (JP-A-10-120795) and the like, but these are methods for measuring luminance distribution at a predetermined scattering angle making use of the angle-dependency of transmitted scattered light of a thin film sample. Some cases of the use of light scattering have been disclosed on the analyses of agarose gel formation process (cf. homepage of Otsuka Denshi, retrieved on Mar. 16, 2002, http://www.photal.co.jp/product/calls-6-1.html) and curd formation process of milk (*Journal of Food Science and Technology* (written in Japanese), vol. 39. no. 4, pp. 309-315). However, these are also on the evaluation of scattering light intensity based on the angle-dependency of transmitted scattered light.

In the conventional techniques, light can hardly penetrate into, for example, a high turbidity material body or a hardly light-permeable or thick massive gel material body or gel-forming sol material body, so that it was difficult to evaluate its angle-dependency of transmitted scattered light. In addition, there were problems in that the samples are limited to thin sections, the device becomes complex for the evaluation of angle-dependency, it is difficult to carry out the measurement on the production line due to a prolonged period of time for the measurement, useful information is deleted depending on the limitation of angle, and the like.

Speckle pattern is a phenomenon in which, when a coherent light forms an image on a rough surface, it complicatedly scatters and interferes with one another depending on the roughness, so that spots having strong brightness (speckles) are generated in a large number as a spatial distribution of irregularly reflecting light, thus forming a spot pattern having contrast (so-called speckle pattern). For example, speckles are removed as a noise in a method in which the structure of a starch dispersion or collagen gel is analyzed by light scattering measurement (JP-A-7-301602). Thus, speckle has been treated as a noise of light and the like electromagnetic wave and supersonic wave, but measurements of displacement, distortion and roughness have recently been introduced as its applied measuring techniques (illustrative examples are not described; "Practical Light Keyword Dictionary" (written in Japanese), published by Asakura Shoten, pp. 202-203). Also, its application to non-contact type migration length (speed) measurement, vibration measurement and the like based on speckle patterns has been devised in a large number. In addition, application of a specific speckle pattern to the recognition of a material or a person has also been devised (JP-A-2000-149087).

On the other hand, the present inventors have recently disclosed a method for discriminating quality of gel shape food or sol shape food (Japanese Patent Application No. 2001-301653), which is a spectral absorption method for evaluating qualities from the absorbance at a specified wavelength of transmitted reflected light.

In this connection, virtually nothing is known about a case in which shapes of formed image or speckle patterns of irradiated light generated by complex scattering and interference of light are employed and applied to the analysis of conditions of gel material bodies and changes thereof, like the invention, and completely no information is available concerning a case in which they were applied to gel shape food or sol shape food (e.g., bean curd (tofu), soybean milk or the like).

Regarding quality of a gel shape material body such as a gel shape food product, its mouth-feel is evaluated generally by synthesizing its physical properties, appearances (shape and color), odor and taste. Particularly, influences of hardness, elasticity and the like physical properties upon the mouth-feel and quality value are great. For example, packed tofu (bean curd) is produced by mixing cooled tofu with a coagulant, filling and packing the mixture and then effecting coagulation of the contents by heating, and too soft, un-coagulated, unevenly coagulated and the like rejected articles are generated on rare occasions due to a change in the soybean quality or an artificial mistake. In addition to this, the same problems are occurring on a large number of polymer gel material bodies.

Regarding material bodies which generate a sol-gel conditional change, a step for changing from sol to gel is contained in the production process of the majority of gel products, and management of the step has been carried out relying on experience and perception of each worker. In case that this step can be objectively measured, it will become useful information on the quality control. In addition, there is a case in which a sol or liquid food article (a drink) becomes a rejected article due to its gelation (coagulation) by an unexpected cause during its processing process or preservation of its package. On the contrary, there is a case in which a material body which formed a gel state become a rejected article due to its conversion into a sol state caused by stirring, external force, heating and the like.

In the case of processed products, exclusive inspectors are carrying out exclusion of rejected articles by sampling inspection (opening the package) or by a feel or with the naked eye without opening. However, in addition to the personnel expenses, in case that a rejected article is shipped to the market by some chance, it will become a claiming problem and cause a danger of incurring serious damages such as reduction of business image and trust, a demand for a large security money, a suspension of business and the like.

In the case of food, hardness, taste and the like qualities are checked by carrying out a destructive test and a sampling test through a sampling inspection as a preventive measure even in the usual quality control, but this cannot be said sufficient because of the problems in that it requires time until the results are obtained, an inspection omission cannot be wiped out and all products of the rejected lot have to be discarded.

However, there is no inexpensive measuring method known in the prior art, for the non-destructive, non-contact, automatic and quick judgment of the qualities of gel state material bodies and material bodies capable of causing changes in the sol-gel state, such as gel-shape food and sol shape food.

In this connection, the speckle pattern is defined as "A complex interference pattern which is formed as a pattern of spots having high contrast in the space when a rough surface is illuminated with a laser beam or the like coherent light, due to interference of lights scattered at respective points on the rough surface with a mutual irregular phase relationship." ("Dictionary of Light" published by Ohm (written in Japanese), pp. 126-127), and "When laser beam is applied to the rough grind surface of paper, frosted glass, a wall, wood, a metal or a plastic material, a pattern of spots which cannot usually be observed shows up. Each spot is generally called as a speckle, and the pattern as a speckle pattern. This pattern is formed, because the lights scattered at respective points on the scattering surface interfere with one another having a irregular phase relationship corresponding to the microscopic irregularity on the surface." ("Optical Measurement Handbook" published by Asakura Shoten (written in Japanese), p. 234).

However, it is described that "Fineness of the pattern is not related to the surface roughness and the like microscopic structures of the surface but determined by the shape and size of irradiated spots on the surface, and the pattern becomes rough as the spots are reduced." and "When pint of the image formation system is turned away from the diffusing surface, the image becomes blurred, but the speckle is clear as usual." ("Optical Measurement Handbook" published by Asakura Shoten (written in Japanese), p. 234).

DISCLOSURE OF THE INVENTION

The object of the invention is to solve the aforementioned problems regarding the quality control of processed products (including packaging products and intermediate products during production processes) by establishing a non-destructive and non-contact type method for the measurement of gel state of a material body and a change in sol-gel state of the material body, and thereby to provide a quick automatic inspection system by which 100% inspection can be carried out easily and inexpensively on the production line.

The present inventors have examined various conditions by actually applying a method for the two dimensional measurement of a reflection type or permeation type scattered light by a coherent light to a gel material body or a material which causes a change in sol-gel state, and found as a result that the image formation and speckle pattern on the irradiation light section are reflecting qualities such as gel state, conditional change from sol to gel, conditional change from gel to sol, concentration, hardness, elasticity, tactile, mouth-feel, viscosity, coagulation deterioration and the like, thereby resulting in the invention.

In addition, the invention was completed by realizing a practically inexpensive, quick, non-contact and non-destructive automatic measuring system which is illustratively equipped with a laser beam irradiation source, a CCD camera or the like two dimensional image recognizing means and a transferring means, can grasp an image or speckle pattern of a laser beam section, image-forming on the aforementioned material body surface or observation surface, as a two dimensional image, and can judge the aforementioned qualities of said material body by analyzing the image data.

That is, the invention comprises the following (1) to (7).

(1) The method for evaluating a gel state or a sol-gel state change of a material body described in claim 1 is characterized in that a gel state or a change in sol-gel state of said material body is evaluated based on the conditions of a light section formed on the image forming surface (shape, light and shade and the like) or conditions of the speckle pattern (contrast, light and shade, spread and the like), using a scattered light observation system which observes, through a two dimensional image recognizing means, a gel shape or gel-forming sol shape material body illuminated with a coherent light.

When a coherent light source (a light capable of performing interference, a light having uniform phase, wavelength, amplitude and the like), such as laser beam, is applied to the aforementioned material body, a reflection (or permeation) scattering of the irradiated light occurs on the incident side surface when said material body is semitransparent to opaque, or on the surface of an opaque member arranged on the backside of the material body (opposite side of the incidence) when it is transparent to semitransparent close to transparent, thus forming an image of the irradiated light, and the image is further formed on the observation surface of the two dimensional image recognizing means which observes the image. Depending on the adjustment of aperture diaphragm, focal point and the like, image formation of light can be effected in a space in front and in the rear of the aforementioned material body surface or aforementioned observation surface, on the side of the image recognizing means. On these image formation surfaces, particularly inside of the image on a light beam surface and periphery thereof, optical path difference, direction, wavelength (frequency), phase and the like are delicately changed in performing complex reflection due to the irregular surface and inside compression, network structure and the like of the material body, and as a result, spots having strong brightness (speckles) are generated by the interference of light and an irregular pattern of light and darkness (speckle pattern) appears. These image formation conditions of light (shape, clearness, brightness, density, light and darkness and the like) and conditions of the speckle pattern (shape, distribution of brightness intensity, density, light and darkness, contrast, clearness, spread and the like) are recognized by a CCD camera or the like image recognizing means which can detect it as a two dimensional image. Preferably, image data of the two dimensional distribution image of scattered light intensity are converted into numerical values (to be referred to as "speckle values" hereinafter) by carrying out an image treatment (binary treatment, edge treatment, moving treatment or the like), a pattern recognition (e.g., use of neural network), relative pattern comparison (e.g., coinciding degree of patterns or intensity changing degree of each picture element of the two dimensional distribution, in two or more of images periodically obtained with very little time difference), total value, average value, variance value and the like statistical analysis treatment, linear differential, quadratic differential or the like multiple differential, or integration, arithmetical operation, logarithmic treatment, Fourier transformation or the like operation treatment. Particularly, contrast of the speckle pattern can be effectively expressed by a multiple differential treatment (e.g., linear differential or quadratic differential treatment). In addition, information on the gel state (compression of network structure, hardness, water holding property or the like) and sol-gel state change (e.g., gelation process, solation process and the like of a polymer such as protein) of said material body can be obtained from the aforementioned speckle values using a relational expression consisting between factors whose correlation was found in advance.

The generation principle of speckle pattern of the invention by reflection (or permeation) light scattering is considered as follows. The reflection (or permeation) scattered light observed by two dimension as described in the foregoing comprises a surface reflection light in which a part of light complicatedly performs irregular reflection depending on the state of the aforementioned material body (colloidal liquid, fine network structure, rough network structure or the like) and a permeation reflection scattered light in which a part of light (particularly from long wavelength side 0.6 μm or more of visible light to near infrared) deeply penetrates into inner part of the aforementioned material body, complicatedly repeats scattering, reflection, refraction, polarization, diffraction, absorption, diffusion and the like depending on the state of the aforementioned material body (including the state of intervening member) and then scatters again on the surface (or the rear face or side face). These scattered lights interfere with each other by causing changes in the traveling direction (by angle-dependency), changes in the phase, changes in the amount of scattered light, changes in the wavelength (frequency) and the like. As a result, a portion having strong brightness (speckle) appears as a form of spots inside of the image formation of light formed on the surface (rear face) and observation surface of the aforementioned material body and the peripheries thereof. It is considered that their contrast, density, light and shade, spread, size of each speckle and the like are changed by the qualities (inner gel structure and colloidal state and fluctuation thereof, and the like) of the aforementioned material body. A stable speckle pattern is obtained by a hard gel in such a state that the gel structure is contained, but the speckle pattern is loose and apt to change by a soft gel or liquid structure, and they can be discriminated by comparing at the same exposure time (e.g., a shatter speed of from release to 1/10,000), because the former becomes a clear image, and the latter an unclear image due to multiple exposure.

In this connection, the observation system to be used in the invention is a system in which an incoming irradiated light at a certain incidence angle θ1 and a reflected (permeated) light at a certain incidence angle θ2 are observed, and the θ1 and θ2 are not particularly limited. According to the invention, it is not a method in which a light diffused at various scattering angles is limited (extracted) to a scattering intensity (brightness) at a certain scattering angle like the conventional method, but is a method which observes the entire image formation broadly formed by a broad range of scattering angles from a certain observation direction. The conventional for restricting to a certain scattering angle is apt to undergo influences by heat fluctuation, structural fluctuation, irregularity of the structure, disturbance vibration and the like, thus causing deletion of useful information, so that this is an unstable and inconvenient measurement in carrying out at the actual production facilities. Contrary to this, the invention observes entire brightness distribution broadly formed by a broad range of scattering angles at one time, so that this is characterized in that it hardly undergoes influences by some extent of the disturbance of scattering angle and scattering direction, it is not necessary to search (scan) optimum scattering angle, accurate focusing is not necessary and it can therefore be directly applied to any object. This is an effective method for material bodies whose irregularity can be predicted, such as a material body of multi-component mixture system, a uneven material body, a material body which generates component separation and a material body having soft and easily warping material and shape.

In addition, also effective is a method for taking away influence of a packaging material or for amplifying or clarifying the spackle phenomenon, by irradiating two or more of coherent lights to a material body. The two or more of coherent lights described in the above are irradiated by arranging two or more light sources having the same or different properties (wavelength, output and the like), or as two or more rays of light by arranging a half-path mirror or the like optical resolution device on the optical path of the light source. For example, speckle values become more clear and stable by irradiating to the same position of a material body at appropriate incidence angles.

The applicable gel shape material body of the invention is a material body which uses water, oil, organic solvent or air as the dispersion medium, and a protein, polysaccharide, resin or the like polymer as the dispersed phase or solute, and is a material body whose final state is a solid or gel. For example, it comprises various materials in the field of food, cosmetics, medicaments, inorganic gels, resins and the like industrial products, living body tissues, agricultural and marine products, liquid crystals and the like, but is generally a material in which a polymer is solidified (or crystallized) by forming a tree-dimensional network-like or beehive-like spongy structure (the voids are under a state of keeping a solvent in spaces of for example from 0.001 to several tens μm). The surface is smooth in appearance but can be regarded microscopically as a roughened surface similar to its inner structure. When the gel network void of the aforementioned material body is approximately from ⅛ or more to 10 times (preferably 1 to 2 times) of wavelength of the irradiated light, it is under a state of roughened surface or rough network and the invention therefore can be applied thereto.

Examples of the gel shape material body include agar gel, gelatin gel, tofu, konnyaku (devil's tongue) jelly and the like gel shape food, gel shape hairdressing, rouge, polymer suction sheet, collagen gel and the like cosmetics, ointment, jelly type cream, silicone gel for cosmetic surgery and the like medicaments and medical supplies, silica gel, soil and the like inorganic gels, plastic products, tires and the like comprising resin gels (polypropylene resin (PP), polyethylene resin (PE), low density polyethylene (LDPE), high density polyethylene (HDPE), polycarbonate resin, polyvinyl chloride resin (PVC), vinylidene chloride resin (PVDC), polyester resin (PET), fluorine resin, acrylic resin, methacrylic resin, polyamide resin (PA), silicone resin, epoxy resin, urethane resin, melamine resin (MF), phenol resin (PF), urea resin (UF), ABS resin, polyacetal resin, polybutylene terephthalate resin, polyether sulfone resin, polyimide resin, polyether ketone resin, polysulfone resin, polyphenylene sulfide resin, polyether imide resin, oxybenzoyl polyester resin, polylactate resin and the like biodegradable plastics, natural rubber, synthetic rubber, composite materials and foaming materials thereof and the like), lacquer, artificial lacquer and the like and processed products thereof (lacquer work, paint and the like), deodorant keeping materials, human eyeballs, skin, intestinal organs, brain and the like living body tissues, rice, soybean and the like cereals, vegetables and fruits, seaweeds, fishes and shellfishes, neat and the like agricultural, marine and stock farm products, leather articles, wood and the like, oil and fat solidified by an oil gelling agent, emulsions, micelles (microcapsules) and the like, in which polymers, proteins, polysaccharides, oil and fat, surface active agents, gelling agents and the like high polymers are solidified by forming a three-dimensional network-like or beehive-like spongy structure. Living body tissue in which a large number of cells are assembled, coacervate by coacervation and the like can also be regarded approximately as a gel structure, and the invention can be applied also to their formation and breakdown.

Examples of the gelling agent include agar, starch, pine resin, oil gelling agents (12-hydroxystearic acid, paraffin wax and the like), crosslinking enzymes (laccase, transglutaminase, tyrosinase and the like, and lipase, protease and the like whose reverse reaction shows crosslinking action) and the like industrial additives which have the action to increase viscosity or gelation and form a three-dimensional structure and crystalline structure, but they are not particularly limited. Other than these, a material which causes sol-gel shifting by heating and cooling, such as a resin, is also included. In addition, a substance which acts upon crystallization of oil and fat like a surface active agent, for example, an emulsifying agent such as polyglycerol fatty acid ester which is a large molecule and has a higher fatty acid side chain, also approximately forms a three-dimensional structure or crystalline structure by acting upon oil and fat and emulsion.

As the sol shape material body which causes a conditional change from sol to gel, most of the sol shape raw materials of the aforementioned gel shape material bodies are applicable. Also applicable is a sol shape material body which is generally liquid (sol) having fluidity and viscosity but has a property to gelatinize by an appropriate stimulus (microbial growth, enzyme reaction, heating, cooling, concentration, drying, still standing, decaying, coagulant addition, photochemical reaction or the like) during its processing or preservation. Its examples include soybean milk, reconstituted soybean milk, soybean milk drinks, high concentration soybean protein solution, raw eggs, albumen, stock material solution of tamago-dofu (steamed egg custard) or thick custard soup, milk and processed milk drinks, agar drinks, raw starch solution and the like sol shape food (drinks), and blood, resin powder material dispersed in a solvent, starch paste and adhesive, oil gelling agent and the like, though not limited thereto. For example, a process in which soybean milk or milk is coagulated, a process in which elasticity of dough or fish meat paste is increased during its aging, and the like are also the subjects which can be evaluated by the invention.

On the contrary, a state in which the aforementioned gel shape material body changes to a sol shape by an appropriate stimulus (agitation, external force, vibration, heating or the like) is also the change in sol-gel state as the subject of the invention. Like a material body which shows thixotropy, this is a material body which changes to a sol shape by an appropriate stimulus (agitation, external force, vibration, heating or the like), and a part of the aforementioned gel shape material bodies correspond thereto. For example, high concentration cooled soybean milk gel, soybean protein gel, agar gel, gelatin gel, pectin gel and the like can be cited. Breakdown of living body cells and tissues and soil showing liquefaction phenomenon by earthquake can also be regarded as the material bodies which change from gel state to sol state.

In addition, it is desirable that the aforementioned material body is a material body in which its inner part is a uniform tissue and the surface layer tissue of the surface or around the surface represents the inner tissue. It may also be a fibrous, filamentous, particulate, massive or the like aggregate. The aforementioned material body may be either transparent (light transmittable) or opaque (light un-transmittable). Particularly, this is effective also for a semitransparent to opaque gel by an embodiment like FIG. 1. When this is transparent, it is desirable to employ an embodiment in which transmitted scattered light is allowed to perform image formation by the aforementioned image recognizing means (FIG. 2) or a light un-transmittable member is arranged on a place where the image formation of transmitted scattered light is effected (FIG. 3). In this connection, regardless that the surface of the member is rough surface or smooth surface, when it is constant, relative comparison can be carried out.

Carry out of the invention can be applied to the final product or an intermediate product thereof in any process or circulation, such as from acceptance of the raw materials to intermediate steps, before and after the packaging step, during storage of the stocks, before and after the transportation and the like, in the production process and circulation of the aforementioned gel shape material body and sol shape material body. Said object material body or image recognizing means may be shifted (600 mm/sec or less, preferably from 400 to 10 mm/sec) at the time of the measurement, but it is desirable to stand still from the viewpoint of reproducibility and safety.

Shape of the aforementioned material body is not particularly limited, and its examples include a cube, a rectangular solid, a column, a cup shape, a spherical shape (e.g., a spherical packed tofu packaged with a bubble gum or the like material), a granular shape, a powdery shape, a massive shape, a plate shape, a fibrous (noodle) shape, a filamentous shape, a yarn shape, a cloth shape, a film shape, a tubular shape, a brow container, a bottle shape, a standing pouch and the like. The presence and absence of packing are not limited too, but in the case of a packed product, it is limited to a case in which it is packed with a packing material having an area where at least a part of a light of specified wavelength region can pass through, arranged on any one of its top face, side face and bottom face.

It is desirable that the aforementioned irradiation light is a light having interference (coherence), monochromaticity and directivity, and a laser beam is generally most suitable. Particularly, a coherent light is apt to cause diffraction, interference and polarization through complex and delicate changes of the phase and wavelength of each reflected beam of light, penetrates into the inner part of the aforementioned material body depending on the wavelength, and forms a pattern of small spots having contrast (speckle pattern) overlapping with an image of the irradiation light section or periphery thereof on the aforementioned image formation surface. Information on the gel state or sol state of a material body can be obtained by this speckle pattern or the image on the irradiation light section.

Regarding the light source for emitting the aforementioned irradiation light, illustratively a semiconductor laser (LD, includes a case in which beams of two or more wavelengths are included) is most small and inexpensive. In addition, two or more light sources having different wavelengths may be constructed in combination to obtain more detailed information. In addition to this, a solid laser (Nd: YAG, Ti: sapphire, Nd: glass and the like), a liquid laser (pigment laser) and a gas laser (He: Ne, Ar, carbon dioxide, excimer laser and the like) can also be used. It is possible to use a light emitting diode (LED) and a stripe type semiconductor laser (SLD), too. Regarding the laser oscillation method, it may be a continuous laser or pulse laser.

Also, in addition to the aforementioned laser beam sources, a mercury arc lamp with a combination of a Fourier transformation lens (coherent treatment), a band pulse filter and the lie optical treatments, a stroboscopic light source, a white light source (a xenon lamp or a fluorescent lamp), a solar light, an incandescent light, a sodium lamp, an infrared light source (a nichrome wire heater, a ceramic heater, a tungsten lamp, a tungsten halogen lamp or the like), an ultraviolet ray lamp, an X ray-generating laser plasma light source and the like can also be used as the aforementioned light source.

Regarding the classification of the aforementioned light source based on its optical axis section shape, a very small point light source, a line light source and surface light source which become the assembly of point light sources (a circle, an ellipse, a spot light source, a square, a ring shape and the like), a multiple line light source and the like can be employed. In addition, a lens (a concavo-convex lens, a Fourier transformation lens or the like), a slit plate (has one or more filamentous holes), a pin hole plate (has one or more small holes), a reflector (a mirror or the like smooth plate, a metal plate or the like rough surface plate or the like) and a light projecting method in which the optical axis section shape is deformed, dispersed and interfered (e.g., the use of a speckle shape irradiation light partially having coherence), limited or transferred by a optical fiber or the like can also be used. Also, adjustment of the quantity of light or limitation of wavelength or polarization may be carried out by an aperture diaphragm, an ND filter, a band path filter, a polar screen, an interference filter or the like, or a spectral means by a diffraction grating or a prism. Shape and size of the optical axis section are not particularly limited with the proviso that they are less than the irradiation area of each product. For example, in the case of small shape products such as gel shape food, gel-formable sol shape food, cosmetics and the like, the spot shape or the like surface light source is preferably from about 0.01 to about 100 mm, most preferably from about 1 to about 10 mm. In addition, both of the width and length of the line light source are not particularly limited too, but a width of from 0.1 to 10 mm and a length of from 1 mm to 1 m are practical.

The aforementioned energy density of light is not particularly limited, but it is suitably 10 W or less and from 10 mW to 1 W. A light of more larger output is used when it is desirable to obtain an output sufficient for effecting its permeation into inside of the aforementioned material body.

Wavelength of the irradiation light may be within the ranges of from 0.15 to 0.4 μm (ultraviolet region), from 0.38 to 0.75 μm (visible region), from 0.75 to 2.51 μm (near infrared region), from 2.51 to 25 μm (mid infrared region) and from 25 to 2,000 μm (far infrared region). However, it is desirable to avoid a strong absorption waveband other than those of dispersion media (e.g., water, an organic solvent and the like), packing materials and dispersed phases (a polymer and the like) which constitute the material body.

The aforementioned image recognizing means for its two dimensional detection may be the naked eye when the irradiation light is visible light region, but in the case of a light of non-visible light region, a two dimensional image recognizing means which can take a photograph of at least a light of the same wavelength range of the irradiation light can be used, and its examples include a CCD (charge coupled device) camera, an MOS type camera, a TV camera, a video camera, an image tube (vidicon), an image intensifier and the like image sensors, a camera for photographing, a digital camera and the like. Also useful are a thermography, a thermocouple, a pyroelectric detector, a bolometer and the like infrared detectors. In addition, a device in which a photodiode, a photomultiplier (photomultiplier tube) and the like are two-dimensionally arranged can also be employed. In this connection, the aforementioned image recognizing means may be constructed by an image recognizing means limited to point shapes (pinpoint, spot and the like) and line shapes (ultra thin shape, thick band shape and the like), or by a scanning shifting means and two or more image recognizing means such that entire or almost entire body can be observed.

The aforementioned image recognizing means may be subjected to the adjustment of the quantity of light by an aperture diaphragm, an ND filter or the like, adjustment of shutter speed (from release to 1/20,000, preferably from 1/250 to 1/10,000), sensitivity and the like image recognizing means, limitation of wavelength by a band path filter, limitation of polarization by a polar screen, an optical treatment by a Fourier transformation lens or the like, or a spectral treatment by a diffraction grating or a prism. Since there is a case in which scattering wavelength and plane of polarization change to some degree as described in the foregoing, it is desirable to receive broad beams of light. In this connection, there is a case in which a polar screen is used for the purpose of controlling irregular reflection from the surface of the intervening member. In any case, they are selected based on image analyzing techniques and online measurement conditions so that the most suitable speckle pattern can be observed.

Regarding the aforementioned relational expression of speckle values and quality evaluation values, a regression expression prepared in advance based on model data (by linear expression or quadratic expression of linear approximate expression by the method of least squares, polynomial by multivariate analysis, logarithmic approximate expression, radical approximate expression, exponential approximate expression, discriminant or the like statistical analysis method), a learning structure of a neuro-computer prepared using teacher data, a theoretical expression by fuzzy logic, a theoretical expression by genetic algorithm and the like are used. By using the relational expression, properties and quality values of a material body can be obtained from the evaluation values of the image formation of irradiation light and speckle pattern. In addition, defective articles can be detected and eliminated on the production line by setting a threshold value.

There are various judging criteria on the gel state or sol-gel state change of a material body as an object of the invention, such as physical values by conventional destructive test, viscometer and the like and subjective evaluation values of shape, fluidity and the like appearances. For example, in the case of tofu, steamed egg custard or the like gel shape food (opaque gel), mainly its physical properties (hardness, elasticity, water holding property, sensuous mouth feel and the like) are large elements which decide its product value and are also the main qualities aimed by the invention. The conventional measurement of physical properties is carried out using a destruction tester, a creep tester, a dynamic viscoelasticity measuring device or the like objective physical property tester or by a subjective sensory test by sampling. The water holding property is evaluated, .for example, by the ratio of loss in weight by centrifugation or spontaneous standing. In addition, appearances (shape, weight, color tone, gloss, texture and the like) can also be exemplified, and a calorimeter, a color-difference meter and glossmeter can be used too. These qualities are influenced by delicate processing conditions such as heating, agitation, time, additive agent and the like. Changes in components are hardly accompanied, but, for example, differences are generated among gel structures, and properties thereof, formed by the denaturation of protein or interactions of polysaccharides and the like (generally a change of a high polymer from its secondary structure to higher-order structure and interactions between high polymers, that is, hydrogen bonding, ion bonding, hydrophobic bonding, S—S bonding, covalent bonding and the like associations and electric repulsion). In the case of tofu for example, formation of a three-dimensional network structure by the association of soybean protein fine particles of approximately from 0.05 to 0.1 μm through coagulation of soybean milk has been observed under an electron microscope (cf. Soybean and Processing Thereof 1" published by Kenkosha, p. 298, "Science of Food No. 29 (1976)" published by Marunouchi Shuppan, p. 43: all written in Japanese). In addition, it has been observed under an electron microscope that the voids of networks of various gels are within the range of approximately from 0.01 to 100 μm.

(2) The method for evaluating gel state and sol-gel state change of a material body described in claim 2 is characterized in that, according to the evaluation method described in (1), the aforementioned material body is a gel shape food article or a gel-formable sol shape food article (includes drinks), and its quality and change in quality are evaluated.

Examples of the gel shape food include tofu, steamed egg custard, custard pudding and the like in which protein, polysaccharides and the like high polymers are solidified by forming a three-dimensional network or beehive structure. Examples of the gel-formable sol shape food (drinks) include tofu, a raw egg liquid, milk and the like which are liquids having fluidity and viscosity but food articles having a property to gelatinize by an appropriate stimulus. In addition, the aforementioned gel shape food also includes food articles which change to a sol shape by an appropriate stimulus, such as yogurt, high concentration soybean protein gel and the like.

Among the gel shape food articles, examples of proteinous gel shape food articles include silk tofu (silk-strained bean curd), packed bean curd, cotton-strained bean curd, yose tofu (oboro tofu) and the like bean curds, dough of fried bean curd such as of thick fried bean curd, nama-age, thin fried bean curd, sushi-age (a thin block of deep-fried bean curd with space for rice), ganmodoki (deep-fried bean curd mixed with minced vegetable and seaweed) and the like, freeze-dried bean curd and dough thereof before and after freezing, sushi-age, thick fried bean curd, nama-age, thin fried bean curd, ganmodoki and the like fried bean curds, yuba (dried bean curd) and yuba-tofu, soybean protein gel, soybean milk yogurt, soybean milk jelly, bean flower and the like processed food articles of soybean (includes domestic soybean, imported soybean, soybean powder thereof, separated soybean protein, concentrated soybean protein and the like), kamaboko (boiled fish paste), chikuwa (fish paste cooked in a bamboo-like shape), age-kamaboko (deep-fried fish paste), hanpen, fish sausage and the like fish paste products, steamed egg custard, boiled egg, custard pudding, chawan-mushi (a pot-steamed hotchpotch), meringue and the like egg products, cheese, yogurt and the like raw milk processed products, gelatin, ham and sausage and the like meat processed food, wheat processed food articles including noodles, fine noodles, Chinese noodles, pasta, raw wheat gluten bread (dried wheat gluten bread), gluten, bread dough, pastes of bakery bread and biscuits and the like and bakery biscuits and the like, buckwheat dough, and jam, chocolate, gumi and the like sweets. In addition, examples of the starch- and polysaccharide-based gel (sol) shape food articles include cake dough such as of goma-dofu (bean custard with ground sesame), konnyaku and konnyaku jelly, tokorolen (agar having needle shape), uirou (sweet starch jelly), sweet bean jelly, rice cracker, kakiyama, cake and the like, and rice cake, goma-dofu, powdered-nut and milk jelly, bean flower and the like jelly shape food articles and the like which use a gelling agent. However, the food articles as the object of the invention are not limited thereto.

The gelling agent is gelatin, agar, curdlan, carrageenan, starch, pectin, locust bean gum, sodium alginate or the like food additive, which is a material having thickening activity or gelling activity and not particularly limited. In addition, tofu causes gelation alone by the addition of an aqueous solution of a coagulant (bittern, magnesium chloride, calcium sulfate, calcium chloride, magnesium sulfate or glucono-δ-lactone), an emulsifying coagulating agent ("Magnesfine TG" manufactured by Kao) or a crosslinking enzyme (transglutaminase; "Activa" Super Curd manufactured by Ajinomoto), and konnyaku by the addition of milk of lime, cheese by a milk coagulating enzyme (rennet) solution and yogurt by a lactic acid bacterium or the like, and soybean protein gel by the heating of a 5 to 20% separated soybean protein aqueous dispersion at 80° C.

(3) The method for evaluating gel state and sol-gel state change of a material body described in claim 3 is characterized in that the evaluation method described in (2) is carried out by intervening a member through which at least a portion of the irradiated light can permeate, between the aforementioned material body and the aforementioned two-dimensional light observation system.

This case is not particularly limited with the proviso that it is a member through which at least a portion of the irradiated light can permeate, intervened between the aforementioned material body and the aforementioned two-dimensional light observation system, for example, when the aforementioned material body as the object is packaged with a packaging material, stored in a tank or fed through a piping, or when the aforementioned light source and the aforementioned two-dimensional image recognizing means are coated. The term "a part" means a part of the member, a partial wavelength of the irradiation light wavelength or a portion of the irradiation light quantity. Also, though there is an influence of the gel structure of the aforementioned member itself, the state of the aforementioned material body can be relatively compared when the conditions are constant. In this connection, it can be mostly ignored when the gel network void of the member is ⅛ or less the irradiation light wavelength.

Examples of the material of the aforementioned member which passes irradiation light through it include glass, quartz glass, wood, paper, polypropylene resin (PP), polyethylene resin (PE), low density polyethylene (LDPE), high density polyethylene (HDPE), polycarbonate resin, polyvinyl chloride resin (PVC), vinylidene chloride resin (PVDC), polyester resin (PET), fluorine resin, acrylic resin, methacrylic resin, polyamide resin (PA), silicone resin, epoxy resin, urethane resin, melamine resin (MF), phenol resin (PF), urea resin (UF), ABS resin, polyacetal resin, polybutylene terephthalate resin, polyether sulfone resin, polyimide resin, polyether ketone resin, polysulfone resin, polyphenylene sulfide resin, polyether imide resin, oxybenzoyl polyester resin, polylactate resin and the like biodegradable plastics, natural rubber, synthetic rubber, paper and the like members, composite materials thereof, laminate materials, FRP materials, fibers, films, plates and the like.

The aforementioned member is used as an inspection window, packaging film, packaging material, coating material or printing material. Optical fiber for propagation, optical lens, band path filter, polar screen, prism and the like auxiliary optical members are also included in the invention. In this connection, in case that the aforementioned irradiation light permeable material and packaging material contact with food, they are limited to the materials approved by the food sanitation law. In addition, limitation of the aforementioned member by thickness varies depending on the intensity, wavelength and the like of the irradiation light, but an irradiation light of from visible light to 2.0 µm in wavelength having an output of 10 W or less can pass through a white silicone rubber of from 10 to 30 mm and a transparent silicone rubber of approximately from 100 to 500 mm, so that any material of several mm or less can be employed.

In the case of the aforementioned material body in which the aforementioned member is packaged with an aluminum deposition material or the like non-light permeable material, the invention cannot be carried out, but it becomes possible by arranging at least a part of a light permeable moiety. In addition, a printing moiety, particularly a black printing moiety, has a large light absorption and hardly permeable into the inner part, but the invention can be sufficiently employed when a black printing ink permeating wavelength of a wavelength region other than visible light is selected. In this connection, regarding influences of scorched marks, fried color, coloring and the like on the surface of the material body, information on the inside of packaged food can be accurately obtained by avoiding their absorption wavelength regions in the same manner. This point is the same on the aforementioned material bodies of non-food systems.

(4) The method for evaluating gel state and sol-gel state change of a material body described in claim 4 is characterized in that, in the evaluation method described in (1), (2) or (3), wave length of the irradiation light is within the range of from visible light (0.38-0.75 µm) to near infrared (0.75-2.51 µm).

When a light of from visible light (0.38-0.75 µm) to near infrared (0.75-2.51 µm) is used as the irradiation light like case of the invention, not only it reaches rough face of the surface but also penetrates into the inner area, so that scattered light reflecting three-dimensional structure of the gel (sol) of more deeper layer can be obtained. In addition, in case that more penetration is preferred, it is desirable to select a light having a wavelength of from long wavelength side of visible light to near infrared region (e.g., from 0.6 to 1.1 µm), in view of the measuring sensitivity, economy and safety.

Particularly in a system containing organic matter, such as food, agricultural and marine products and living bodies, there is an absorption wavelength region from 0.6 to 1.1 µm, which is considered to be a secondary overtone absorption of the bonding of solutes (protein, polysaccharides and the like). When an irradiation laser beam having this range is used, influence of water as the solvent is small, and it penetrates into more deeper layer (several mm to several 10 cm from the surface layer), so that scattered light reflecting the state of the inner gel structure can be obtained. Since very complex scattering is repeated, a speckle pattern having more clear contrast can be obtained easily, in comparison with the surface scattered light (cf the principle of speckle pattern generation in the aforementioned paragraph number 0019). For example, in the case of packed tofu, almost all of its inner portion, approximately 100 mm in depth from the surface layer of the measuring face, at least from 1 to 50 mm, can be evaluated by a laser beam having a wavelength of from 0.6 to 1.1 µm (output 1 W).

In the case of tofu (or soybean milk) for example, easily absorbable wavelength is mainly from 0.6 to 1.3 µm, and a wavelength of this range easily penetrates into the inner portion so that the invention can be carried out easily. In addition, the absorption wavelength of polypropylene containers is a broad range of from 0.6 to 2.0 µm, and longer wavelength becomes difficult to be absorbed. Accordingly, it is desirable to select a wavelength of within the range of from 0.6 to 1.3 µm for the tofu in a polypropylene container. In this connection, a wavelength of 1 µm or less is practical from the viewpoint that an inexpensive image recognizing means having sensitivity to that region can be employed. However, when an inexpensive system can be realized in response to the future technical advance, it may not be limited to these wavelengths.

However, in case that the aforementioned material body has a particularly high water content (e.g., a water content of 60% by weight), there are large absorbance of water (e.g., 1.2 µm, 1,45 µm, 1.94µ and the like in the long wavelength infrared region, and there are influences of the atmospheric temperature and infrared radiation, so that it is desirable to avoid it to the best. In addition, it is desirable to the best to avoid absorption wavelengths of members blocking the aforementioned material body, such as a packaging material, a printing paint and the like, and outer skin tissues (scorching, staining). In this connection, ultraviolet rays are absorbed by plastic and glass product materials, and infrared rays are absorbed by glass product materials.

In addition, it becomes unnecessary to set the aforementioned scattered light observation system in a dark room, by avoiding emission wavelength of stray light such as of natural light, interior illuminations (fluorescent light, mercury light) and the like. In this connection, when influence of stray light is avoided, it is desirable to select a wavelength region by avoiding the emission wavelengths of visible light region and outer light sources (fluorescent light, mercury light and the like).

In general, the near infrared region is minutely divided generally into 3 sections of a wavelength region 1 (combination tone region) of from 1.8 to 2.51 µm, a wavelength region 2 (primary overtone region) of from 1.4 to 1.8 µm and a wavelength region 3 (secondary overtone region) of from 0.75 to 1.1 µm. It has been reported that the use of the wavelength region 3 having high permeability is desirable in the case of the measurement of chemical components, particularly suited for a food article having a water content of 80% by weight or more (Tetsuo Sato, Abstract of Papers, 5th Non-destructive Measurement Symposium, pp. 8-14; Iwamoto and Uozumi, Japanese Society of Food Science and Technology, vol. 32, no. 9, pp. 685-695). According to the invention, the long wavelength side of visible light also has the same property of the aforementioned near infrared wavelength region 3, so that the range of from 0.6 to 1.1 µm as described in the foregoing is desirable as the wavelength capable of carrying out the invention.

(5) The method for detecting free water in gel shape packaged food described in claim 5 is characterized in that, in the evaluation method described in (2), (3) or (4), free water presenting in the inner part (measuring surface) of a product which passed a step for contacting with water after sealed packaging of the aforementioned material body is detected, for example, in case that it is a defective product in which water is soaked into its inner part due to pin hole, cracking, insufficient sealing and the like on the packaging material or in case that release of water is generated due to low water holding property of the gel.

In this connection, any method can be employed as a method for contacting a packaged product with water, such as methods for soaking in a steam heating tank, hot water tank, cooling water tank or the like, carrying out water jet showering or spraying with water or steam.

This invention is based on the fact that the speckle pattern is abnormally stressed and becomes clear (increase of speckle values) due to further increased complex refraction of the aforementioned reflection type scattered light when a thin water layer is present between a packaging film and a gel material body. Though a dedicated pin hole detector of vacuum type or electric system is on the market, the invention is valuable in view of the point that it can be measured together with the inner qualities.

(6) The method for evaluating gel state and sol-gel state change of a material body described in claim 6 is a method for carrying out the evaluation method described in (1), (2), (3), (4) or (5), which is a method for evaluating a material body characterized in that the aforementioned material body is made into a dynamic state. This is a method in which, when made into the aforementioned dynamic state, a speckle pattern or the like image is observed by an image recognizing means while applying a micro-vibration, excitation, reciprocation, sound wave, supersonic wave, air- or water-spraying or the like external force continuously or intermittently, or just after termination of the external force. The inertia force when a material body is moved, accelerated, decelerated or stopped on a conveyor can also be used. In addition, a very little vibration by a pulse laser can also be used. Since the change in speckle pattern by dynamic state differs depending on the hardness or softness of the gel state or sol state material body, it becomes easy to obtain correlation with hardness (breaking force).

The ultrasonic oscillator has a frequency of 20 kHz or more, preferably from 20 to 50 kHz, and an output of 0.2 W/cm$^2$ or more and 100 W/cm$^2$ or less, preferably from 0.5 to 10 W/cm$^2$, and the ultrasonic vibrator is arranged, for example, by contacting to a conveyer on which the objective material body is mounted or to the objective material body. In addition, it is possible to take an embodiment in which the material body or its bearer (a conveyer or the like) is vibrated or reciprocated in the mono-axial direction, biaxial direction or tri-axial direction. As the vibration apparatus, any one of a magnetic system, excitation system, pneumatic system, hydraulic system and the like methods can be used. Frequency of the vibration is from 5 to 5,000 Hz, displacement is from 10 to 5,000 μm, speed is from 1 to 10,000 mm/s, acceleration is from 1 to 100,000 m/s$^2$ and impact vibration power is from 0.5 kN to 30 kN, but preferably, the frequency is from 5 to 400 Hz, displacement is from 20 to 500 μm, speed is from 10 to 200 mm/s and acceleration is from 20 to 1,000 m/s$^2$ (7) The device described in claim 7 for carrying out a method for evaluating gel state and sol-gel state change of a material body is a device for carrying out the evaluation method described in (1), (2), (3), (4), (5) or (6), characterized in that the aforementioned material body constituting at least one row in the transverse direction against a moving direction, the aforementioned light irradiation device which irradiates a light having at least one spot shape or line shape section traversing the moving direction (this may be fixed to or separated from a light irradiation photographing device prepared by arranging at least one of the aforementioned two-dimensional image recognizing means) or at least one of them is moved by a moving means, thereby carrying out scanning measurement of almost full face or full face of the aforementioned material body.

In this connection, the moving means is not particularly limited with the proviso that it can effect relative movement of the aforementioned material body and aforementioned light source. Regarding the two dimensional image recognizing means, there is a case in which it is fixed alone to photograph whole body of the aforementioned material body or a case in which it is fixed with a light source and simultaneously moves, but in any case, the invention can be employed when it is a method capable of scanning and photographing the full face or almost full face.

The moving method may be a continuous, intermittent or the like method and is not particularly limited. In addition, as shown in FIG. 10 to FIG. 13, the aforementioned material body may be standing still or flowing in a container, a tank, a piping or the like.

In the case of an automatic measurement, for example, primary differential values of the brightness of respective picture elements (e.g., differences in the brightness of respective picture elements adjoining in the traverse direction or values obtained by dividing the differences by inter-picture element distances are totaled, the calculation is repeated in the longitudinal direction, and then all values are totaled) is calculated on the two-dimensional image data obtained from the speckle pattern and image formation of irradiated light (about 10 milliseconds as the required time for 1 measurement, a very short period of time of from 1 millisecond to 100 milliseconds per 1 performance including times for data communication and calculation treatment). The above measurement is continuously repeated twice or more, preferably 10 to 50 times, and the average value of the calculated values obtained by respective measurements is used as the result of one measurement. Particularly, clearness and contrast of the speckle pattern can be expressed by the primary differential values. A system for outputting quality indexes of a material body, discriminating rejected articles or excluding them from the line by an exclusion means is assembled, based on the aforementioned relational expression prepared from the numerical values obtained by the calculation treatment and separately measured quality index values of the material body. Since such a system is a non-destructive, non-contact, inexpensive and quick system, 100% inspection can be carried out at a high speed on the production line.

Thus, according to the invention, the measuring time is markedly short which is 1 to 2 seconds or less, generally from several 10 to several 100 milliseconds. Even when there is a change in the aforementioned material body, such as a scattered light angle-dependent or thermal fluctuation or a static fluctuation accompanied by a structural irregularity, such a change within the measuring time is almost negligible. Even in case that there are some influences, it is not necessary to take them into consideration because they are treated by averaging them. In addition, even when the scattering angle is changed in each measurement to some extent, it is a degree of somewhat changing the position of speckles, so that only a very little influence is exerted upon contrast and the like of the speckle pattern.

In the actual measurement in the field, a period of time is required until the observed values are stabilized, due to vibration of machines in the surroundings, swaying of the aforementioned material body and the like. In general, the measurement is carried out twice or more, preferably 10 to 100 times, under such a state that the observed values are stable, and an average value (or an intermediate value) of the thus obtained aforementioned speckle value data, if necessary after excluding abnormal values, maximum value, minimum value and the like, is used as the central value. In case that the measurement is carried out by repeating two or more of the measurement, the duration becomes from 10 milliseconds to 10 seconds. In addition, by deducing final observation value from the observation value increasing rate or accelerating rate until the aforementioned observation values become stable, one measuring time can be further shortened so that a high speed measuring system can be constructed.

Figure 1:
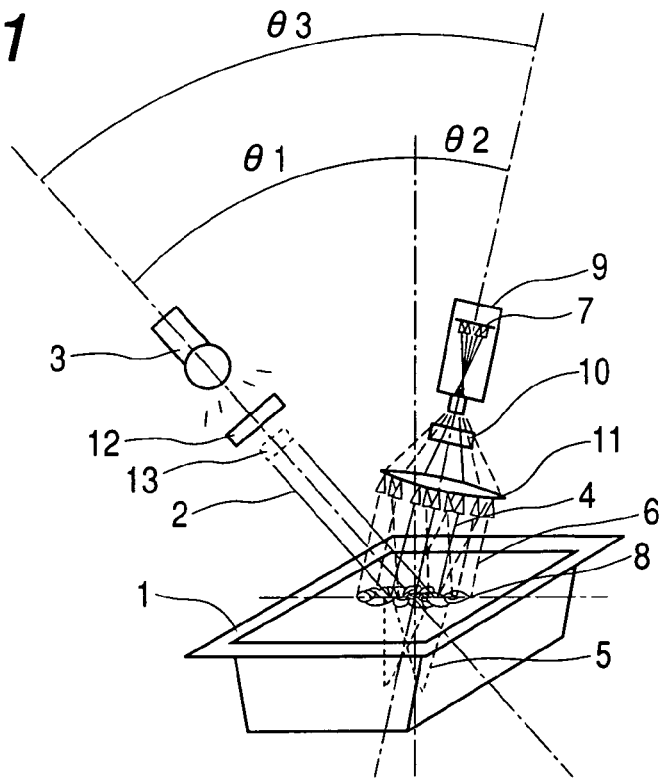
FIG. 1 is an explanatory drawing of the two-dimensional observation system of reflection type scattered light described in claim 1 and Example 1 of the invention (image formation on the surface of the aforementioned material body was photographed)

Regarding the reference numerals and signs in the drawings, 1 is a material body, 2 is a coherent irradiation light, 3 is a light source, 4 is a surface reflection type scattered light, 5 is a permeation reflection type scattered light, 6 is a speckle pattern, 7 is an image formation on the observation surface, 8 is an image formation on the material body surface, 9 is two-dimensional image recognizing means, 10 is an aperture diaphragm, polar screen, band path filter or the like optical auxiliary part, 11 is a condenser lens, diffusion lens or the like optical auxiliary part, 12 is a Fourier transformation lens, polar screen, band path filter or the like optical auxiliary part for optical transformation or limitation use, 13 is a line, spot or the like optical axis transformation lens, slit plate or the like optical auxiliary part for optical axis shape transformation or limitation use, 14 is a device for agitation use, 15 is a container (box) for a gel shape material body or a material body capable of causing a gel-sol state change, 16 is a container (tank) for a gel shape material body or a material body capable of causing a gel-sol state change, 17 is a container (piping) for a gel shape material body or a material body capable of causing a gel-sol state change, 18 is an inspection hole, 19 is a moving means, 20 is an image of linear irradiation light, 21 is an optical fiber for irradiation light use, 22 is an optical fiber for image light (light interception) use, 23 is a tuning conveyer, 24 is a main body (detecting element) conveyer, 25 is a shake off conveyer, 26 is an operation control panel, 27 is a shake off device, $\theta 1$ is an angle of incidence (vertical line on the contact surface of incident light axis and irradiation site of an object to be treated, so-called angle of normal line), $\theta 2$ is an angle of reflection (transmission) (vertical line of light-intercepting light axis on the contact surface of reflection site of an object to be treated, so-called angle of normal line), A is a moiety of a speckle pattern having strong contrast (hard), and B is a moiety of a speckle pattern having weak contrast (soft).

BEST MODE FOR CARRYING OUT THE INVENTION

As shown in FIG. 1, the principal part of the embodiments described in claims 1 to 7 of the invention is constituted by a two-dimensional scattered light observation system equipped with a light source 3 which applies a coherent light 2 to the aforementioned material body 1 at angle of incidence $\theta 1$ (e.g., $0° \leq \theta 1 <$ critical angle $< 90°$) and a two-dimensional image recognizing means 9 that observes a surface reflection type scattered light 4 emitting from the surface of the aforementioned material body 1, a permeation reflection type scattered light 5 once permeated into the inner part and again reflected therefrom and an interference speckle pattern 6, at an angle of reflection (permeation) θ2 (e.g., 0≦θ2≦180°). The observation angle is 0≦θ3≦180°.

In the case of the measurement of reflected light, the angle of incidence θ1 is generally 0°θ1<90° (provided that θ1 <critical angle, and strictly, θ1 is adjusted such that it becomes smaller than the critical angle determined by respective index of refraction at the interface between air and a packaging material and at the interface between the packaging material and the inner material body), preferably 20°≦θ1<70°, and the angle of reflection (permeation) θ2 is 0°≦θ2<90°, preferably 0°≦θ2<70°. In some cases, it is desirable to avoid total reflection. Total reflection occurs when normal line is contained in the face composed of the incidence light axis and light-intercepting light axis, and θ1=θ2. The observation angle θ3 is 0≦θ3<180°, preferably 20°≦θ3<140°.

In the case of the measurement of transmitted light, the angle of incidence θ1 is 0°≦θ1<90° (θ1<critical angle), preferably 20°≦θ1<70°, similar to case, and the angle of reflection (permeation) θ2 is 0°≦θ2<180°, preferably 20°≦θ2<180°. The observation angle θ3 is 0≦θ3<180°, preferably 20°≦θ3<180°. Permeation measurement of θ1=0° and θ2=0° is similar to the reflection measurement but, for example, is a case in which the incidence light axis and light-intercepting light axis are parallel and the incidence site and light-intercepting site are different from each other.

It is also effective to change the light 2 emitted from the light source 3 into an appropriate coherent light via the Fourier transformation lens, polar screen, band path filter, reflecting mirror (smooth surface or rough surface), photorefractive crystal filter, interference filter (obscure glass, a resin, a gel shape material, a colloid particle dispersion or the like) or the like optical auxiliary part 12 for optical transformation or limitation use, or the line, spot or the like optical axis transformation lens, slit plate or the like optical auxiliary part 13 for optical axis shape transformation or limitation use.

It is also effective to process or limit the light interception (image) via the aperture diaphragm, polar screen, band path filter or the like optical auxiliary part 10 or the condenser lens, diffusion lens or the like optical auxiliary part 11, before the two-dimensional image recognizing means 9.

Figure 2:
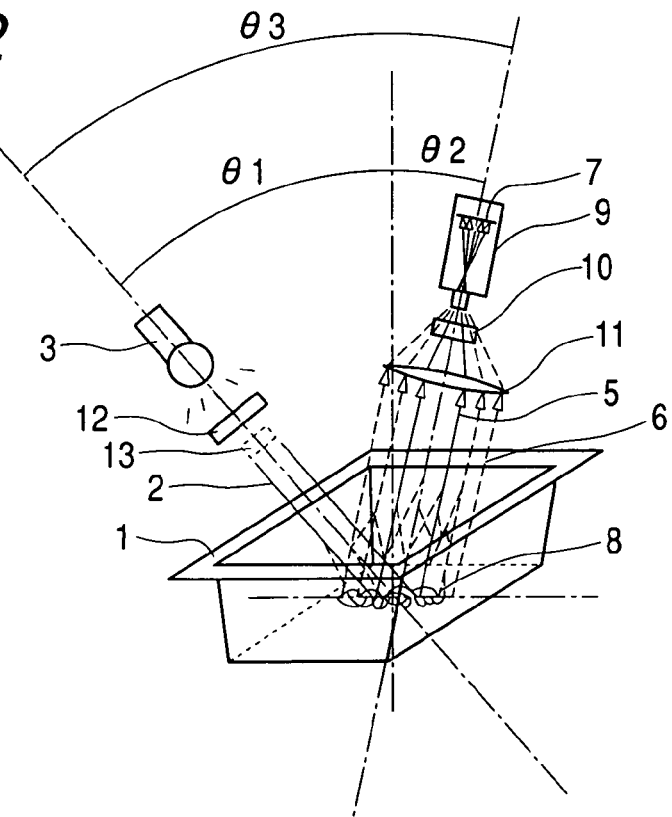
FIG. 2 is an explanatory drawing of the two-dimensional observation system of reflection type scattered light described in claim 1 and Example 1 of the invention (image formation on the rear face of the aforementioned material body was photographed)
Figure 3:
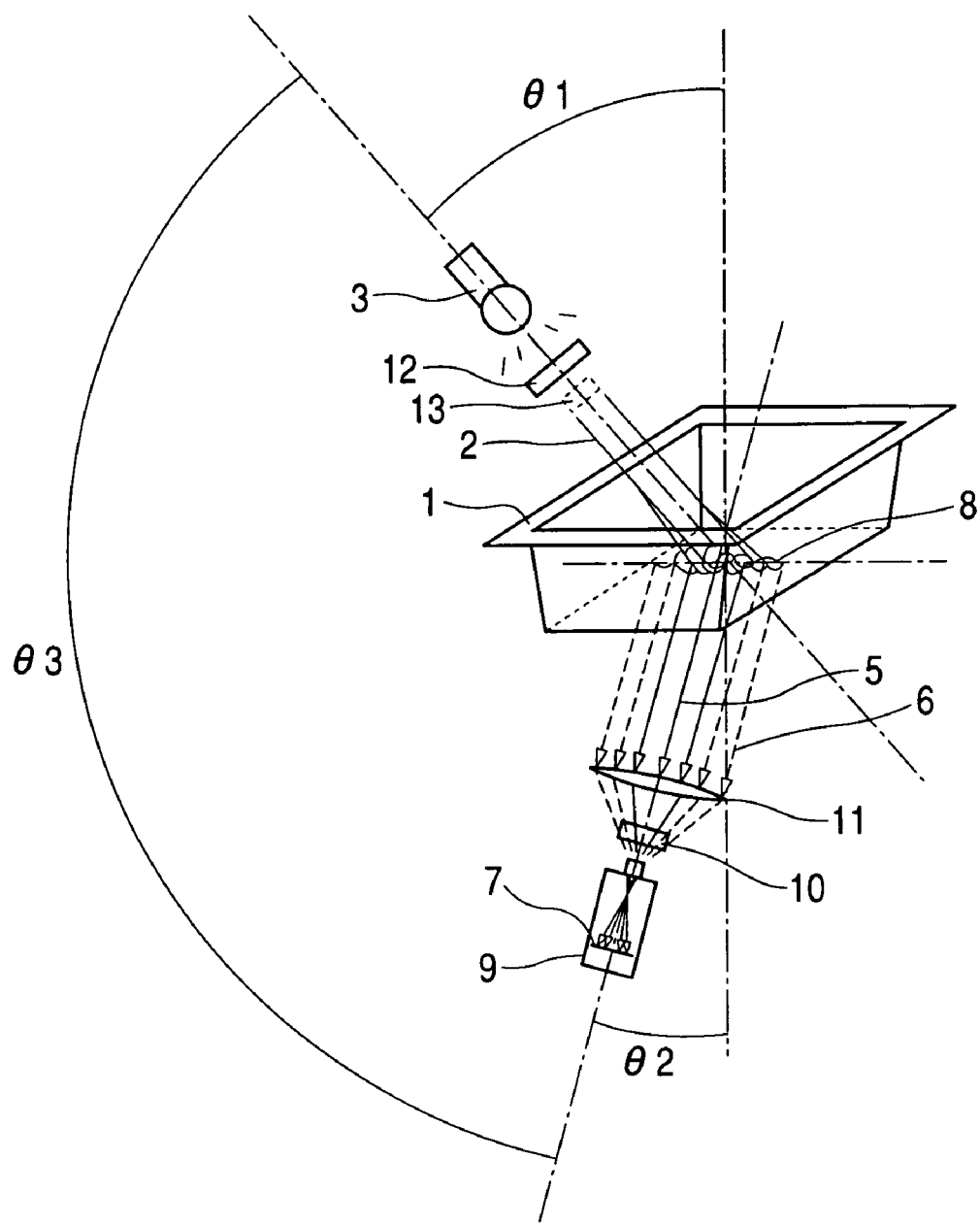
FIG. 3 is an explanatory drawing of the two-dimensional observation system of permeation type scattered light described in claim 1 of the invention (image formation of scattered light permeated trough the aforementioned material body on the rear face was photographed)

The aforementioned surface reflection type scattered light 4 is an irregular reflection light scatters at random on the material body surface (diffused reflection light, not related to the angle of incidence θ1) and causes mutual and complicated interference with the permeation reflection type scattered light 5 when a light penetrates into inside of the aforementioned material body to cause complex transmission, scattering, refraction, dispersion (spectral action), diffraction or polarization and again scatters at the angle of reflection (transmission) θ2, and as a result, the image formation 8 on the material body surface (upper surface on the material body in FIG. 1, or lower rear face on the material body in FIG. 2 and FIG. 3), image formation 7 on the observation surface or speckle pattern 6 is formed. In this connection, θ2 may not always the same as θ1. In addition, the embodiments of FIG. 2 and FIG. 3 are embodiments which can be carried out particularly when the material body is semi-transparent to transparent.

Figure 13:
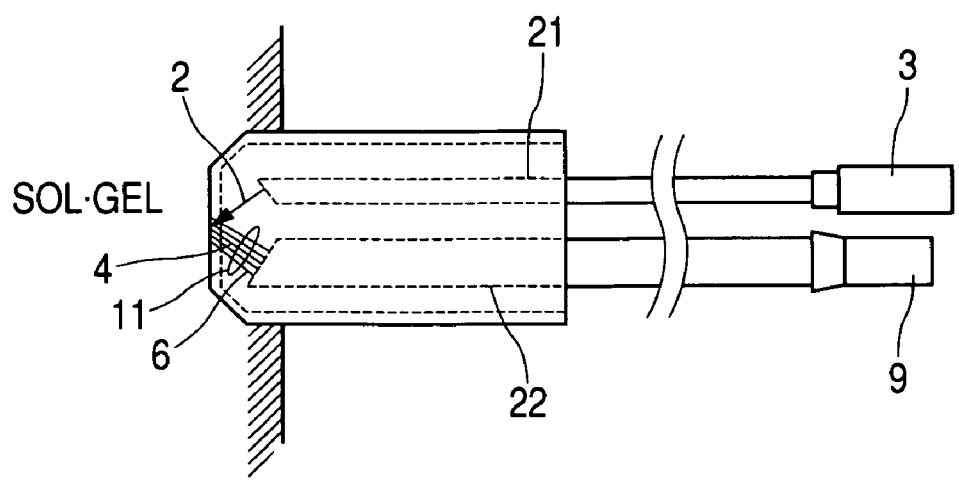
FIG. 13 is an explanatory drawing of the sol-gel state change measuring embodiment (probe system sensor) described in claim 1, claim 2, claim 3 and Example 4 of the invention.

Regarding the aforementioned two-dimensional image observation system, it is possible to employ an optical fiber-mediated embodiment due to the necessity to carry out remote measuring for the explosion-protection and drip-proof purposes or an embodiment as a small probe shape which directly contacts to the aforementioned material body (FIG. 13), in addition to an embodiment in which the laser beam source 3 and the CCD camera 9 for example are arranged in the space on the aforementioned material body. In these cases, a form in which the aforementioned two-dimensional image observation system is coated with a irradiation light-transmittable member is desirable. This can be applied to inline measurement, explosion-protection, drip-proof and the like purposes and is one of the embodiments of the invention, and though being a liquid-contacting type, this can be regarded as a non-contact means mediated by the aforementioned member.

Examples of qualities which are not the object of the invention include generally shapes (size, weight, missing and the like), taste and the like chemical quality items. It is possible to construct a synthetic quality measuring system by combining with other optical, chemical and physical methods.

On the other hand, in carrying out the invention, a phenomenon was found in which the brightness (or absorbance or reflection light quantity) and shape of the image formation 8 of the irradiation light section on the material body surface are changed by the concentration (concentration of solid contents) of the aforementioned material body. That is, light and shade (concentration of solid contents) of the aforementioned material body can be predicted from the changed amount of its image. For example, in case that the image formation 8 of the irradiation light section is an ellipse, the image formation gradually becomes circular and then an unclear shape as the concentration of solid contents increases. Useful information can be simultaneously obtained also from the image formation of the irradiation light section in combination with the speckle pattern.

In addition, in carrying out the invention, another phenomenon was also found in which, when the aforementioned material body is an O/W or W/O type emulsion having a turbid state of water phase and oil phase, the brightness and shape of the aforementioned image formation itself by irradiation light or the speckle pattern are changed in response to its emulsion dispersion condition and particle size distribution. That is, particle size distribution and particle size change in the aforementioned material body can be measured based on the changed quantity. For example, the speckle pattern of irradiation light shows clear contrast when rough particles are frequent, and an unclear pattern is observed in the case of fine particles. Conventionally, in carrying out measurement of a thick emulsion by particle size distribution measurement based on a transmitted light scattering method, there was a disadvantage in that its state is somewhat changed due to the necessity to dilute it with a solvent. By applying the invention, state of a thick emulsion can be monitored directly or real time.

EXAMPLES

Figure 20:
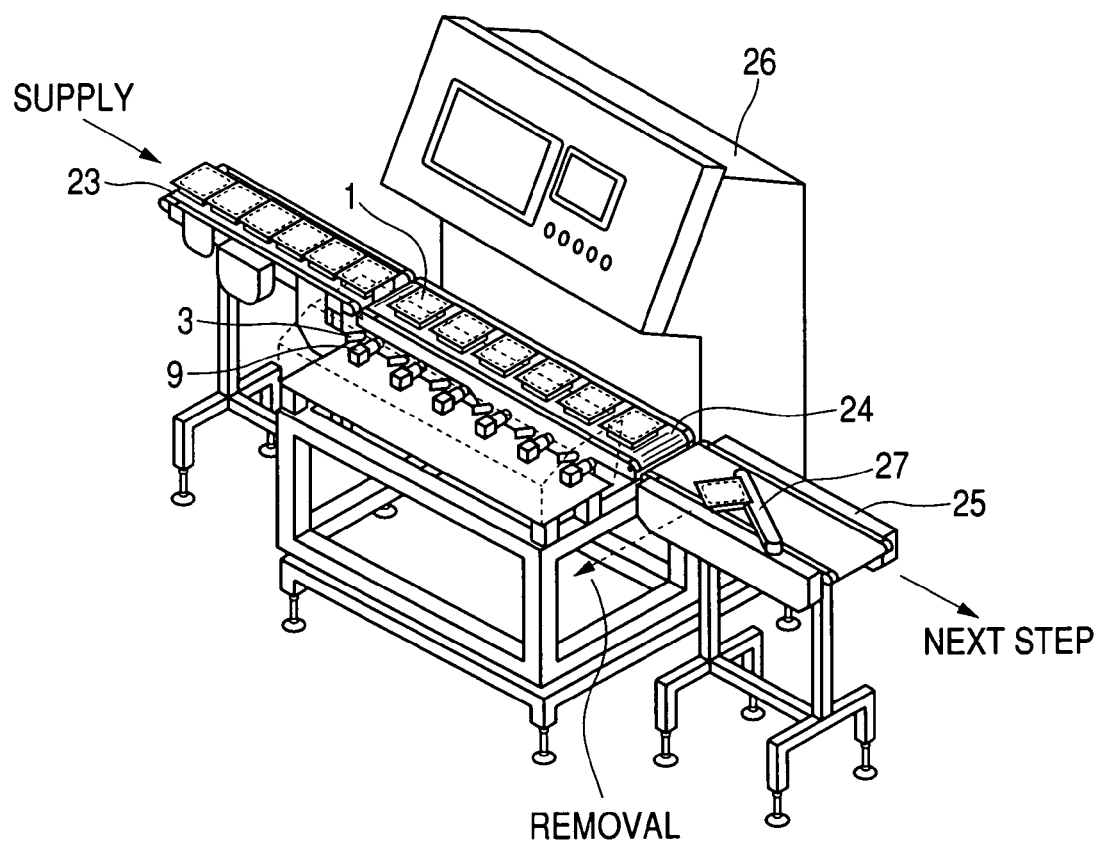
FIG. 20 is an explanatory drawing of an inspection device system into which a two-dimensional observation system of reflection type scattered light was built, described in claims 1 to 7 and Examples 1 to 7 of the invention.

The invention can be carried out, for example, by the embodiment shown in FIG. 20. This is constituted from a tuning conveyer 23, a main body (detecting element) conveyer 24, a shake off conveyer 25 and an operation control panel 26, the light source 3 and image recognizing means 9 are arranged in one set or more in the main body, and for example, the material body of object is received from a supplying-transferring conveyer by a stopper of the tuning conveyer 23 and transferred to the main body conveyer 24, and then, for example, light from the light source 3 is applied to a side face of the material body of object and its image is image-photographed by the image recognizing means 9, thereby effecting the measurement. At the time of the measurement, said material body of object 1 may be moved (600 mm/sec or less, preferably 400 mm/sec), but it is desirable to allow it to stand still in view of reproducibility and stability. After the measurement, samples are transferred from the main body conveyer 24 to the shake off conveyer 25, and a material body whose measured result was judged, for example, good (a gelatinized article or coagulated article) proceeds to the next step, but a material body judged as a defective article (an un-gelatinized article or un-coagulated article) is eliminated by the shake off device 27. Adjustable setting of the treating capacity can be made, for example to a number of from 1,000 to 10,000 samples per 1 hour, by controlling the number of material bodies to be transferred to the main body conveyer 24, conveyer speed and the like. In addition, it is possible to correspond to from a thinning inspection to the 100% inspection when light sources and cameras are arranged in response to the number of samples. In this connection, the embodiment of FIG. 20 is an example of the embodiments of the invention and not particularly limited thereto.

The laser beam source 3 is a semiconductor laser (MLX manufactured by KMKO GIKEN, oscillating power 30 mW, spot light is an ellipse of 3×6 mm, no lens head, and the irradiation wavelength is for example 0.67 µm, 0.78 µm, 0.82 µm, 0.85 µm or the like), which was applied to the surface of the aforementioned material body at a angle of incidence of about 30°. As the two-dimensional image recognizing means 9, a CCD camera (XC manufactured by SONY, 1 picture element 10 µm, 350,000 picture elements, and a light intercepting wavelength of from visible light to near infrared region was used) was used and light interception on the surface of the aforementioned material body 1 was effected at an angle of reflection of about 0°. This was focused on the image forming surface 8 of irradiation light, namely on the surface of the aforementioned material body in the case of a semi-transparent to opaque gel as shown in FIG. 1, or on the rear face of the aforementioned material body in the case of a transparent gel as shown in FIG. 2. In this connection, a darkroom condition was not employed for particularly shutting out the outdoor daylight in carrying out the photographing, and the measurement was carried out under an interior light. Regarding the speckle pattern 6 of the thus obtained image data, an average value of the total value of differential values obtained by 30 times of the measurement was used as the speckle value as described in the foregoing. Correlation analysis, multiple regression analysis and analysis of variance were carried out on the relationship between this speckle value and the conventional analytical values using a commercially available statistical analysis software (EXCEL 2000 manufactured by Microsoft, or the like) to obtain a multiple regression expression and an approximate expression.

In this connection, the light source and image recognizing means and the calculation methods for data treatment and numerical treatment are not limited thereto.

Various conditions were examined in the invention, and found that the aforementioned speckle value has a high correlation with the gel state or sol-gel state change of material body. That is, examination was made on the correlation between speckle values under sol state, gel state, sol-gel intermediate state and the like various states and fracture force value, concentration, mouth feel and the like qualities. As a result, the contrast became clear and the speckle value became large as the gel became hard, thus showing a high coefficient of correlation. Also, a semi-mature or sol state gel showed a blurred speckle pattern and therefore can be easily distinguished with the naked eye from a hard gel. In the same manner, there was a tendency to show the speckle pattern in broader range, and the contrast strongly, during the process of changing from a sol state to a gel state, and further from a soft gel state to a hard gel state. Also, a relationship was found between the average value of brightness which represents light and shade of speckle pattern and the hardness, obtaining a result that the darker, the harder. In addition, there was a tendency that shape of the image formation of an oval irradiation light section becomes close to complete round, for example, as the solid content of a gel becomes large.

The following describes Examples which used the two-dimensional image recognizing systems of scattered light as shown in FIG. 1 and FIG. 2, on a packed tofu prepared by mixing a cooled soybean milk with a coagulant, filing and packaging the mixture and then heating it to effect coagulation, a hot packed tofu prepared by mixing a hot soybean milk with a coagulant and then filing and packaging the mixture, an albumen gel, a gelatin gel, an agar gel and a coffee-containing carrageenan gel as examples of the gel shape material body, and a polyethylene resin as an examples of the resin.

Example 1

Regarding the gelatin gel, 0, 3.5, 8.8, 17.5 or 35 g of a gelatin powder (an article on the market) was weighed, swelled with a small amount of water, adjusted to a total volume of 350 ml by adding boiling water, dissolved by stirring and filled in a semi-transparent pack made of PP (2B size, 300 ml capacity), and then the pack was heat-sealed with an NY/PP film and put in a refrigerator overnight to effect gelation.

Regarding the agar, 0, 0.17, 0.34, 0.86, 1.75 or 3.5 g of an agar powder (an article on the market) was weighed, adjusted to a total volume of 350 ml by adding boiling water and then gelatinized in the same manner as the case of gelatin.

Regarding the carrageenan gel, 0.17, 0.34, 0.86, 1.75, 3.5 or 7 g of a carrageenan powder (manufactured by Okuno Seiyaku) was weighed, mixed with 1.5 g of a soluble coffee powder (an article on the market), adjusted to a total volume of 350 ml by adding boiling water and then gelatinized in the same manner as the case of gelatin.

Regarding the albumen gel, 3.5, 8.76, 17.5 or 35 g of an albumen powder (manufactured by Okuno Seiyaku) was weighed, adjusted to 350 ml by adding cool water and then subjected to 1 hour of heat coagulation in a water bath controlled at 80° C. This was cooled with ice water and then refrigerated overnight.

Figure 4:
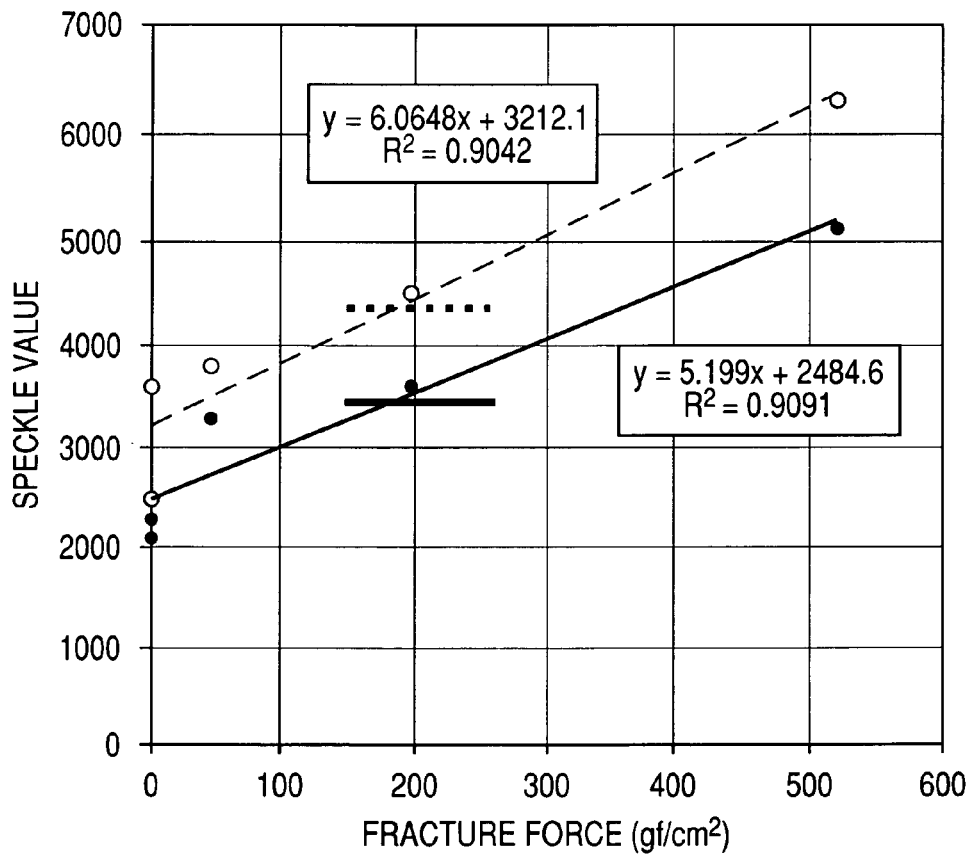
FIG. 4 is an explanatory drawing on the relationship between hardness of a gelatin gel and speckle value (observed value) described in claim 1 and Example 1 of the invention.
Figure 5:
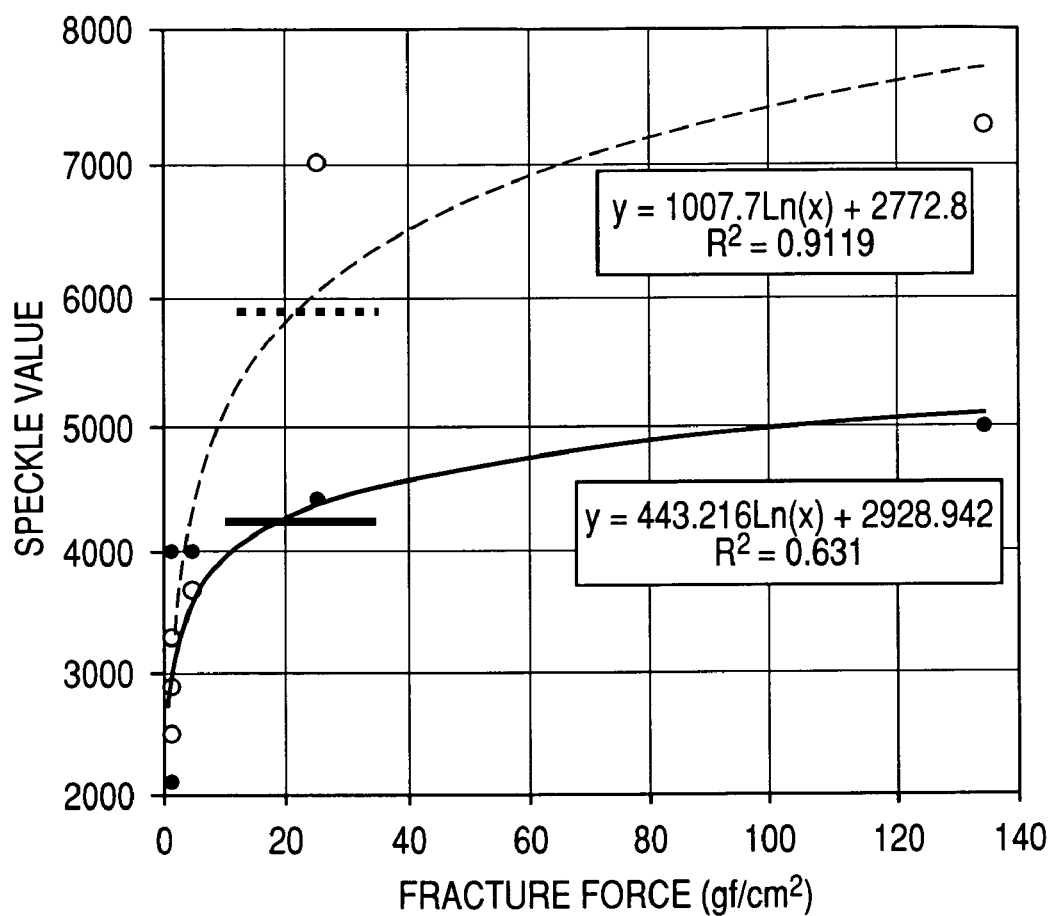
FIG. 5 is an explanatory drawing on the relationship between hardness of an agar gel and speckle value (observed value) described in claim 1 and Example 1 of the invention.
Figure 6:
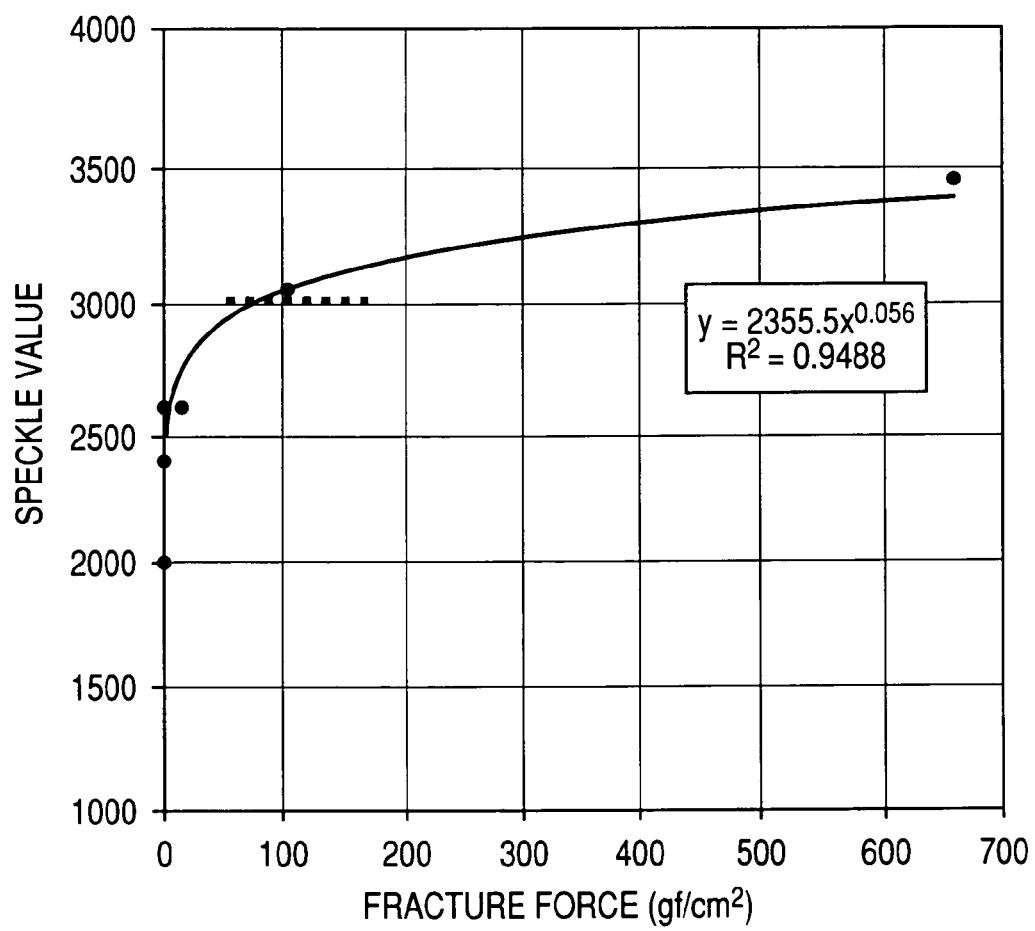
FIG. 6 is an explanatory drawing on the relationship between hardness of a coffee-containing carrageenan gel and speckle value (observed value) described in claim 1 and Example 1 of the invention.
Figure 7:
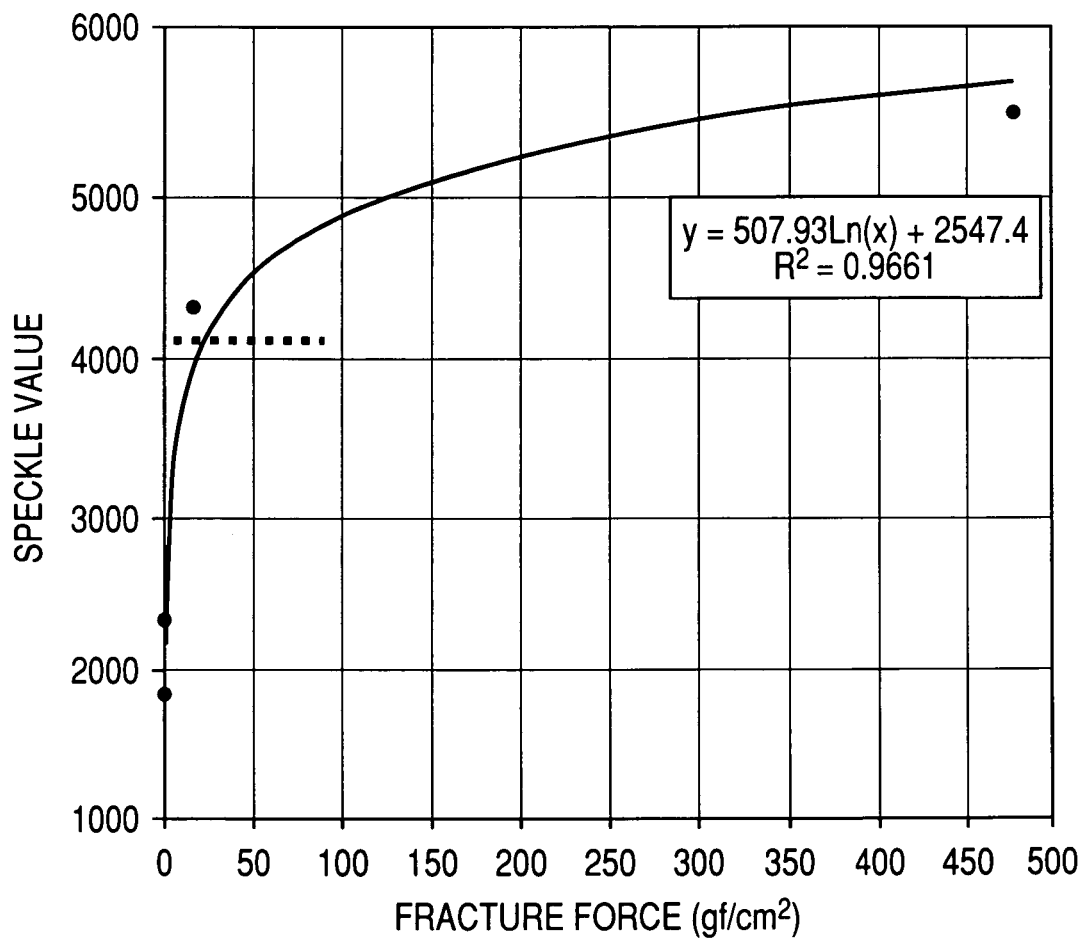
FIG. 7 is an explanatory drawing on the relationship between hardness of an albumen gel and speckle value (observed value) described in claim 1 and Example 1 of the invention.

Each gel sample was allowed to stand still with the film face or container bottom face upward (pack surface), and the speckle pattern 6 was observed using the semiconductor irradiation light 2 of 0.67 µm in wavelength and using the aforementioned scattered light two-dimensional observation system (FIG. 1). Thereafter, each sample was unsealed and, as it is in the container, subjected to the measurement of fracture force (a 23 mmϕ plunger is penetrated at a speed of 6 cm/min, and the stress at the time of fracture is measured) using a rheometer (NRM-2002J, manufactured by Fudo Kogyo). The results are shown in Table 1 and FIG. 4 (gelatin gel), FIG. 5 (agar gel), FIG. 6 (coffee-containing carrageenan gel) and FIG. 7 (albumen gel).

TABLE 1

| Concentration | Fracture force | Speckle value | |
|---|---|---|---|
| % | gf/cm² | Pack surface | Pack rear face |
| Gelatin gel | | | |
| 10.0 | 519.5 | 5100 | 6300 |
| 5.0 | 197.4 | 3600 | 4500 |
| 2.5 | 47.2 | 3300 | 3800 |
| 1.0 | 1.0 | 2300 | 3600 |
| 0.0 | 0.0 | 2100 | 2500 |
| Agar gel | | | |
| 1.0 | 134.8 | 5000 | 7300 |
| 0.5 | 25.9 | 4400 | 7000 |
| 0.2 | 4.8 | 4000 | 3700 |
| 0.1 | 1.0 | 4000 | 3300 |
| 0.0 | 1.4 | 2500 | 2900 |
| 0.0 | 1.0 | 2100 | 2500 |
| Coffee-containing carrageenan gel | | | |
| 2.0 | 662.1 | | 3450 |
| 1.0 | 105.9 | | 3050 |
| 0.5 | 17.5 | | 2600 |
| 0.2 | 3.9 | | 2600 |
| 0.1 | 0.5 | | 2400 |
| 0.0 | 0.1 | | 2000 |
| Albumen gel | | | |
| 10.0 | 478.5 | | 5500 |
| 5.0 | 16.7 | | 4330 |
| 2.5 | 0.5 | | 2340 |
| 1.0 | 0.5 | | 1840 |
| Polyethylene resin | | | |
| Ultra high density | hard | | 27620 |
| High density | slightly hard | | 25930 |
| Expanded | soft | | 13950 |

On the other hand, using commercially available polyethylene resins, namely an ultra high density polyethylene resin (molecular weight 3,000,000 or more; UHMW), a high density polyethylene resin (molecular weight 1,000,000 or more; HMW) and an expanded polyethylene resin (B-4; slightly soft), their smooth surfaces were directly observed to measure speckle values in the same manner, with the results shown in Table 1. In this connection, it can hardly be expressed by figures, the speckle pattern of UHMW was fine, and that of HMW was rough, when their image states were observed. Based on this, the invention can also be applied to the evaluation of compression density of polymers.

In the case of the gelatin gel, measured values from the film face and pack bottom face were different, but it was able to obtain respective linear regressions showing high correlation with their fracture forces (pack surface: y=6.0648x+3212.1, coefficient of determination 0.9042, pack rear face: y=5.199x+2484.6, coefficient of determination 0.9091) (y: speckle value, x: fracture force value).

In the case of the agar gel, high correlation with fracture force was obtained from the pack rear face than the film surface (pack rear face: y=1007.7Ln(x)+2772.8, coefficient of determination 0.9119). In the case of the coffee-containing carrageenan gel, y was $2355.5x^{0.056}$ and coefficient of determination was 0.9488 in the pack rear face. In the case of the albumen gel, y was 507.93 Ln(x)+2547.4 and coefficient of determination was 0.9661 in the pack rear face.

In this connection, it was possible also to distinguish gels having sufficient hardness from semi-mature to un-coagulated gel (sol) based on the threshold values shown by continuous or broken horizontal lines in FIG. 4 to FIG. 7.

Example 2

A powdered soybean slurry namago prepared by dispersing 7 kg of finely powdered domestic soybean (manufactured by Dauichi Tanpaku) in 35 kg of water for about 20 minutes using a dispersing machine (KD50-MS, manufactured by Takai Seisakusho) was boiled (5 minutes, 102° C.) using a soybean milk production plant (NS2000S, manufactured by Takai Seisakusho) without adding antifoaming agent and then passed through a wringer (Sirius Single String manufactured by Takai Seisakusho, a water flea collecting net: 150 mesh) to obtain about 40 kg of a soybean milk having a soybean milk concentration of 11.5% brix. This was cooled with ice water until use.

A 3 kg portion of the soybean milk (10° C.) was weighed and mixed with a coagulant solution prepared by mixing 0, 6.7, 13.4 or 15.2 ml of a 1:1 by weight bittern solution of a field bittern (manufactured by Akaho Kasei) with 3 g of a protein crosslinking enzyme ("Activa" Super Curd manufactured by Ajinomoto) and adjusting the total volume to 50 ml with water, and the mixture was immediately filled in a pack for tofu (white Kyo type, material PP, 350 g) and packaged with a film (material NY/PP, no printing). As a blank, a sample was also prepared by filling and packaging the soybean milk alone. Thereafter, this was heated in a hot water bath of 60° C. or 80° C. for 35 minutes and then cooled to be used as a measuring sample. In this case, another sample was also prepared by heating a sample of 13.4 ml of the field bittern only at 60° C. for 35 minutes.

Each of the samples under the packaged state was allowed to stand still with its film face upward, and the speckle pattern 6 by the irradiation of the laser beam 2 of 0.78 μm was photographed (measured) using the aforementioned two-dimensional image recognizing system of the scattered lights 4 and 5. By carrying out the measurement 30 times for one test, primary differential values of the brightness of speckle pattern were calculated, and the average value of 30 times was used as the speckle pattern value.

Figure 8:
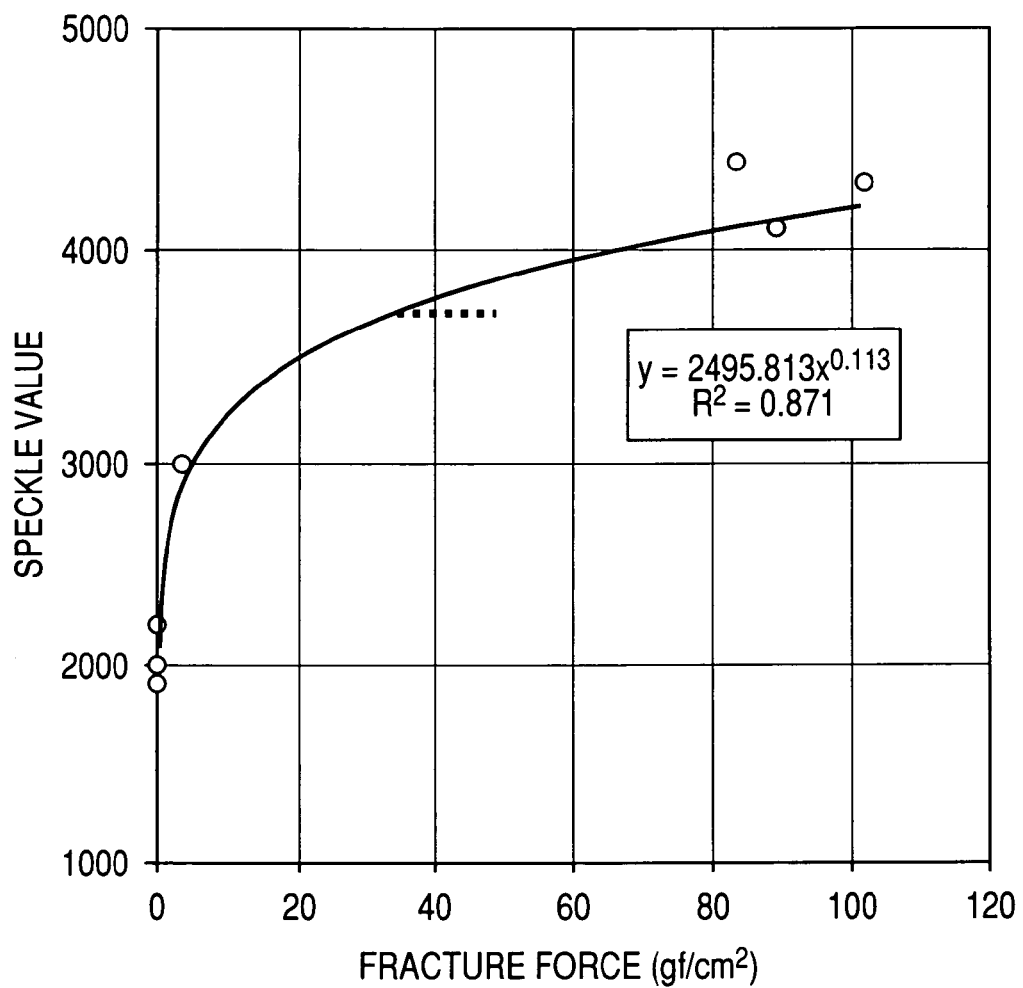
FIG. 8 is an explanatory drawing on the relationship between hardness of a packed tofu and speckle value (observed value) described in claim 1 and Example 2 of the invention.

Thereafter, each sample in the container after peeling off the film was subjected to the measurement of fracture force using a rheometer (NRM-2002J, manufactured by Fudo Kogyo), sampling evaluation (appearance, color, odor, taste and texture are scored by 10 steps, and the total is expressed as points out of possible 100) by several panelists and measurement of water release ratio based on the difference in weights before and after 2 hours of standing. The results are shown in Table 2 and FIG. 8.

TABLE 2

| | | No mark | 0 | 1 | 2 | 3 | 4 | 5 |
|---|---|---|---|---|---|---|---|---|
| Bittern addition ratio | % | 0.00 | 0.00 | 0.00 | 0.11 | 0.22 | 0.22 | 0.25 |

TABLE 2-continued

|  |  | No mark | 0 | 1 | 2 | 3 | 4 | 5 |
|---|---|---|---|---|---|---|---|---|
| Field bittern (1:1) | g | 0.0 | 0.0 | 0.0 | 6.7 | 13.4 | 13.4 | 15.2 |
| Water | g | 50.0 | 0.0 | 50.0 | 43.3 | 36.6 | 36.6 | 34.8 |
| Enzyme addition ratio | % | 0.00 | 0.00 | 0.10 | 0.10 | 0.10 | 0.10 | 0.10 |
| Fracture force | gf/cm$^2$ | 0.5 | 0.5 | 0.0 | 3.9 | 83.3 | 89.4 | 102.1 |
| Average water release ratio | % | 0.0 | 0.0 | 0.0 | 0.0 | 12.3 | 2.9 | 11.1 |
| L |  | 79.9 | 79.9 | 79.5 | 80.5 | 82.6 | 82.2 | 83.2 |
| a |  | −6.7 | −6.7 | −6.7 | −6.6 | −6.5 | −6.8 | −6.6 |
| b |  | 15.3 | 15.5 | 15.2 | 15.3 | 15.0 | 14.8 | 14.9 |
| Tofu pH |  | 6.65 | 6.66 | 6.67 | 6.50 | 6.34 | 6.37 | 6.31 |
| Product evaluation |  | soy milk | soy milk | soy milk-like | semi-mature | hard | spring, soft | hard |
| Speckle value |  | 2000 | 1900 | 2200 | 3000 | 4400 | 4100 | 4300 |

Regarding the hardness (fracture force) which is important for determining tofu quality, there was a high correlation between it and speckle value. When the fracture force was represented by x, and the speckle value by y, a radical approximate expression y=2495.813x$^{0.1013}$ (coefficient of determination 0.871) was derived. In addition, as shown by a broken horizontal line in FIG. 8, it was able to distinguish completely coagulated non-defectives from semi-mature or un-coagulated defectives based on a speckle value of about 3800 as the threshold value.

Example 3

Beans of a domestic soybean Toyomasari (produced in Hokkaido in 2000) were soaked in well water at 15° C. for 22 hours. A 17.6 kg portion of the soaked soybeans corresponding to 8 kg of raw soybeans were pulverized, and the thus prepared namago was mixed with 40 g of an antifoaming agent (Emulsy Super manufactured by Riken Vitamin) and boiled (5 minutes, 102° C.) using a soybean milk production plant (NS2000S, manufactured by Takai Seisakusho) and then passed through a wringer (Sirius Single String manufactured by Takai Seisakusho, a water flea collecting net: 100 mesh) to obtain about 35 kg of a soybean milk having a soybean milk concentration of 13.0% brix.

Figure 9:
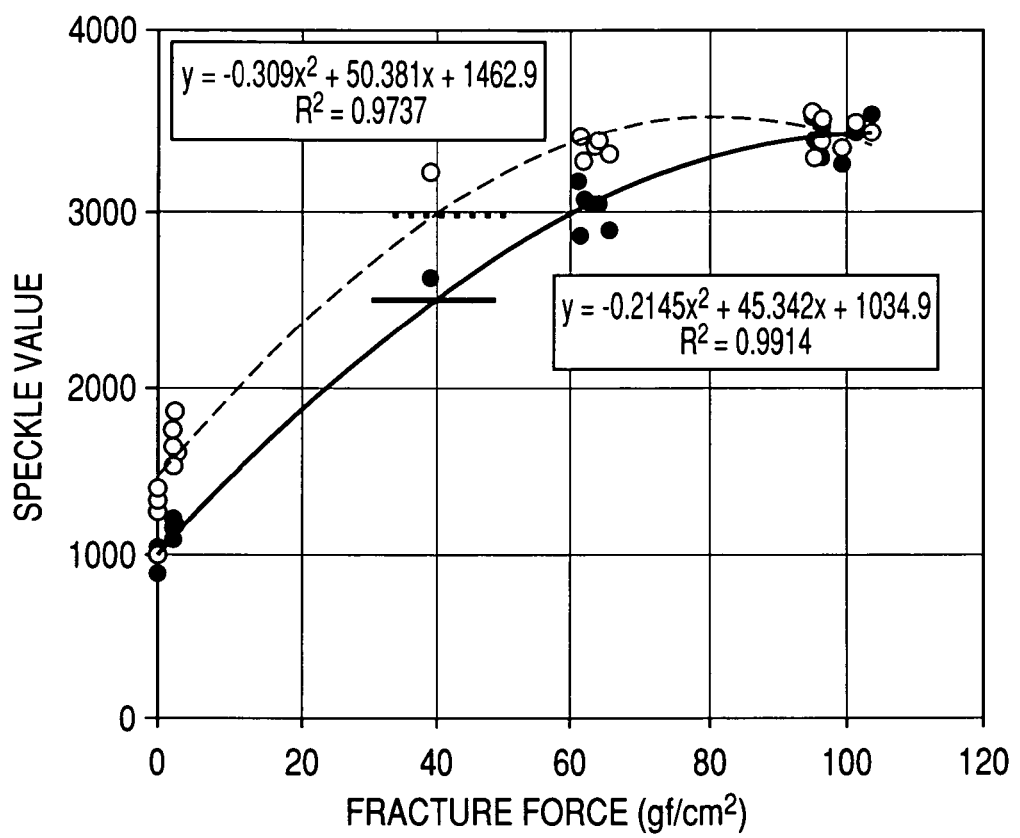
FIG. 9 is an explanatory drawing on the relationship between hardness of a hot packed tofu and speckle value (observed value) under packaged state and unsealed state described in claim 2 and Example 3 of the invention.

The soybean milk was controlled at 82° C. in a soybean milk tank and pumped out by a metering pump (a rotary pump manufactured by Nakakin) and, on the other hand, an emulsion bitter (MagnesFine TG manufactured by KAO) was pumped out by a precise metering pump (Mono-Pump manufactured by Heishin) at a rate of 0, 1, 2 or 3 L/H, both of them were combined by a piping system and immediately subjected to a strong dispersion using a static type mixing and stirring device ("TS Mixer" manufactured by Takai Seisakusho) and then immediately thereafter, the dispersion was filled in a pack for tofu (Kyoto type 350 g, PP) and packaged with a film (NY/PP). Immediately thereafter, using the samples still warm under packaged state and the samples under unsealed state by peeling off the packaging films immediately thereafter, speckle values were measured in the same manner as described in the aforementioned Example 2. The results are shown in Table 3 and FIG. 9.

TABLE 3

| Emulsion bitter flow rate | Sample | Speckle value | | Fracture force |
|---|---|---|---|---|
| L/h | n = 26 | Packaged state | Unsealed state | gf/cm$^2$ |
| 0.0 | 1-3 | 871 | 1259 | 0.0 |
|  | 1-4 | 1040 | 1012 | 0.0 |
|  | 1-5 | 904 | 1345 | 0.0 |
|  | 1-6 | 1055 | 1403 | 0.0 |
| 3.0 | 2-1 | 3498 | 3399 | 97.1 |
|  | 2-2 | 3536 | 3435 | 103.9 |
|  | 2-3 | 3518 | 3549 | 95.2 |
|  | 2-4 | 3391 | 3283 | 95.3 |
|  | 2-5 | 3287 | 3504 | 96.5 |
|  | 2-6 | 3248 | 3337 | 99.6 |
|  | 2-7 | 3427 | 3482 | 101.5 |
|  | 2-8 | 3488 | 3512 | 96.6 |
| 2.0 | 3-1 | 3067 | 3274 | 62.1 |
|  | 3-2 | 3158 | 3409 | 61.3 |
|  | 3-3 | 3049 | 3369 | 63.7 |
|  | 3-4 | 2863 | 3408 | 61.6 |
|  | 3-5 | 2888 | 3313 | 65.7 |
|  | 3-6 | 3054 | 3382 | 64.5 |
|  | 3-7 | 2616 | 3208 | 39.0 |
| 1.0 | 4-1 | 1224 | 1710 | 2.2 |
|  | 4-2 | 1187 | 1612 | 2.8 |
|  | 4-3 | 1195 | 1742 | 2.2 |
|  | 4-4 | 1192 | 1529 | 2.1 |
|  | 4-5 | 1142 | 1748 | 1.9 |
|  | 4-6 | 1165 | 1857 | 2.4 |
|  | 4-7 | 1098 | 1644 | 2.2 |

Although there was a slight difference between the cases of the presence and absence of the packaging film, there was a high correlation between the fracture force and the speckle value. When the fracture force was represented by x, and the speckle value by y, the multinomial approximate expression was y=−0.2145x$^2$+45.342x+1034.9 under the packaged condition, and the coefficient of determination was 0.9914. Under the unsealed condition, the multinomial approximate expression was y=−0.309x$^2$+50.381x+1462.9, and the coefficient of determination was 0.9737. In addition, as shown by solid and broken horizontal lines in FIG. 9, it was able to distinguish completely coagulated non-defectives from semi-mature or un-coagulated defectives based on a speckle value of about 2500 under packaged condition, and a speckle value of about 3000 under unsealed condition, as respective threshold values.

Example 4

Figure 10:
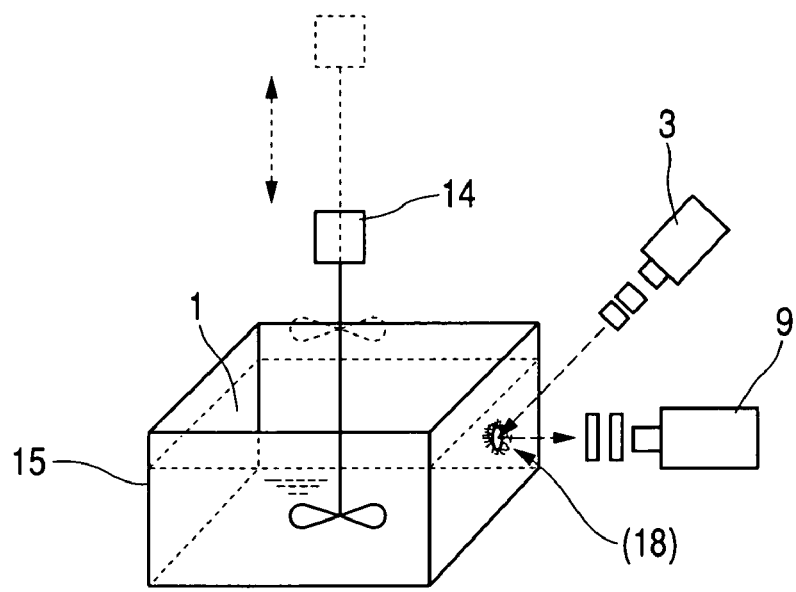
FIG. 10 is an explanatory drawing of the sol-gel state change measuring embodiment (box type, small scale batch system) described in claim 1, claim 2, claim 3 and Example 4 of the invention.

As shown in FIG. 10, the aforementioned scattered reflected light two-dimensional observation system can monitor gelation process of the contents and gelation condition of the contents. Practically, coagulation process of a soybean milk was periodically measured.

A 12 liter portion of a hot soybean milk 1 (13% brix, 70° C.) prepared as described in Example 3 was put into a polypropylene container box 15 (370×370×depth 150 mm, board thickness 10 mm) and, under the following coagulation conditions, continuously monitored by the two-dimensional image observation device 9 from the start of the coagulation agitation, by arranging the scattered reflected light-observing two-dimensional observation system as sown in FIG. 10 on the side face of the aforementioned container box and irradiating the light 2 from the semiconductor laser beam source 3 at a wavelength of 0.82 μm, and speckle values with the lapse of time were measured starting from the addition of each coagulant at every 1 second for 20 minutes (average of 30 measurements); on the case of the addition of 36 g of GDL (glucono-δ-lactone, manufactured by Fujisawa Pharmaceutical) dispersed in 200 ml of water, on the case of the addition of 120 g of transglutaminase ("Activa" Super Curd manufactured by Ajinomoto, contains 0.2% transglutaminase) dispersed in 200 ml of water, on the case of the addition of 36 g of a clear powder (calcium sulfate, "Pearl α" manufactured by Akaho Kasei) dispersed in 200 ml of water or on the case of the addition of 96 g of a liquid bittern (crude sea water magnesium chloride, "Umino Megumi" manufactured by Takai Seisakusho, contains 33.2% magnesium chloride), while stirring the milk with the batch type coagulation device 14 ("MultiCurdy Type S" manufactured by Takai Seisakusho), or on the case of the addition of 120 ml of an emulsion bittern ("Magnesfine TG" manufactured by Kao, contains 33% magnesium chloride) dispersed using a using a static type dispersion device ("TS Mixer" manufactured by Takai Seisakusho), effected by using a continuous coagulation device ("New Curdy" manufactured by Takai Seisakusho). A process displaying the results for every 20 seconds is shown in FIG. 14.

In this connection, a stainless steel container box having an inspection hole 18 of a material which can transmit irradiation light may be used as the container box 15. In addition, when the liquid face is in a static state, the surface of soybean milk or the surface of tofu may be directly observed.

Figure 11:
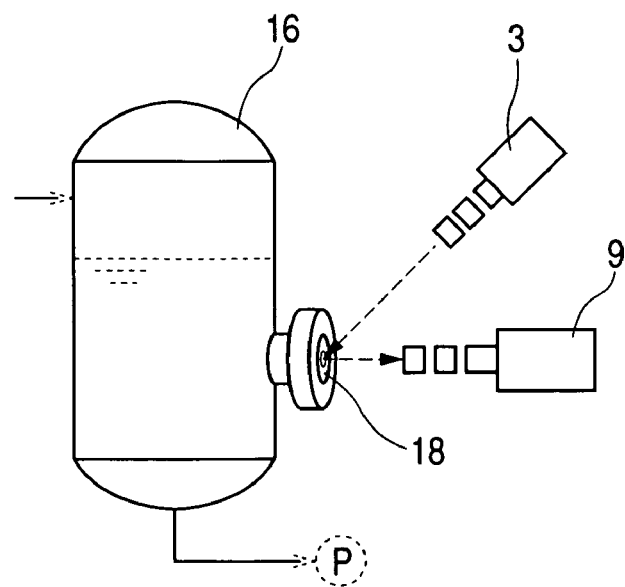
FIG. 11 is an explanatory drawing of the sol-gel state change measuring embodiment (tank, large scale batch system) described in claim 1, claim 2, claim 3 and Example 4 of the invention.
Figure 12:
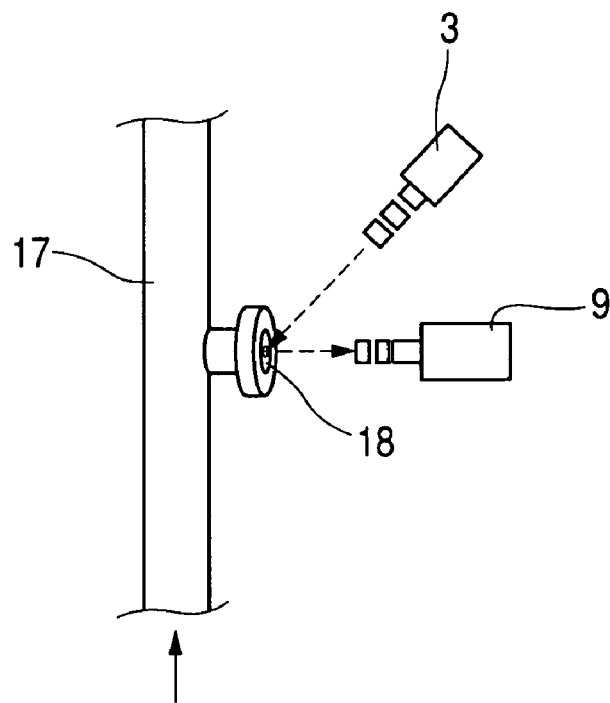
FIG. 12 is an explanatory drawing of the sol-gel state change measuring embodiment (piping, inline continuous system) described in claim 1, claim 2, claim 3 and Example 4 of the invention.
Figure 14:
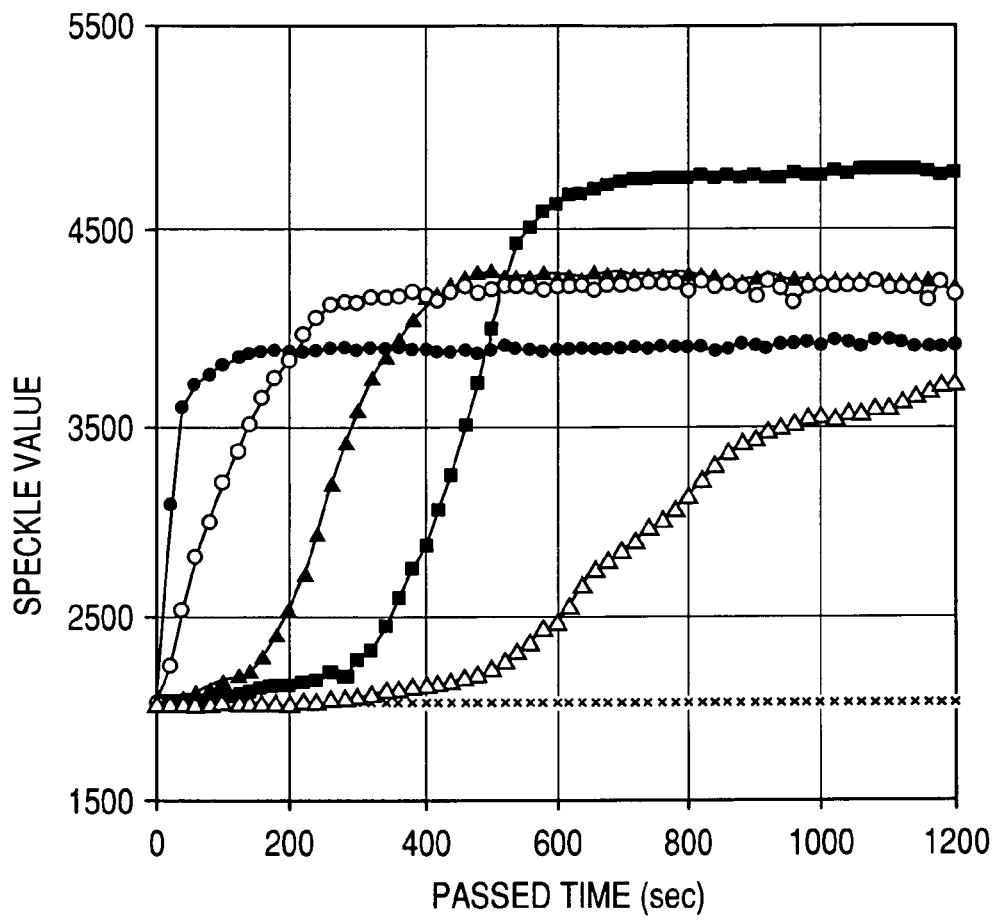
FIG. 14 is an explanatory drawing on the speckle value (observed value) which changes by the gelation step and gel state of a gel formable sol shape food article, described in claim 3 and Example 4 of the invention.

As shown in FIG. 14, the reaction rate of coagulants (coagulation gelation rate of soybean milk) coincided with the order of coagulation rate known by experience in the conventional tofu production, which was liquid bittern>emulsion bittern>clear powder>GDL >transglutaminase. Also, the values under finally stabilized condition reflected relative differences of the hardness of tofu, namely in order of GDL>clear powder≅emulsion bittern>liquid bittern>transglutaminase, and well coincided with their relationship with the fracture force values obtained in the same manner as described in the forgoing after subsequent water bleaching in a water tank. In this connection, this example can be carried out also by the tank having an inspection hole shown in FIG. 11 or the piping shown in FIG. 12 and FIG. 13.

Example 5

Samples of the hot-packed tofu prepared in the foregoing (Example 3) in the case of perfect heat-sealing of film and in the case of partially imperfect sealing were cooled in a water tank and then measured using the aforementioned scattered reflected light-observing two-dimensional observation system. As a result, the speckle value was about 3500 in average in the former case, but the latter case showed an abnormally high value of from 5000 to 6000. Accordingly, it was found that a pin hole can be detected. In addition, when the amount of coagulant in the aforementioned hot-packed tofu was increased by adding an excess amount of 1.5% of the emulsion bittern to soybean milk, the speckle value after aging showed a slightly high value of from 4000 to 5000 in the same manner, so that it was able to detect a condition of excess coagulation, so-called "yorisugi".

Example 6

Figure 19:
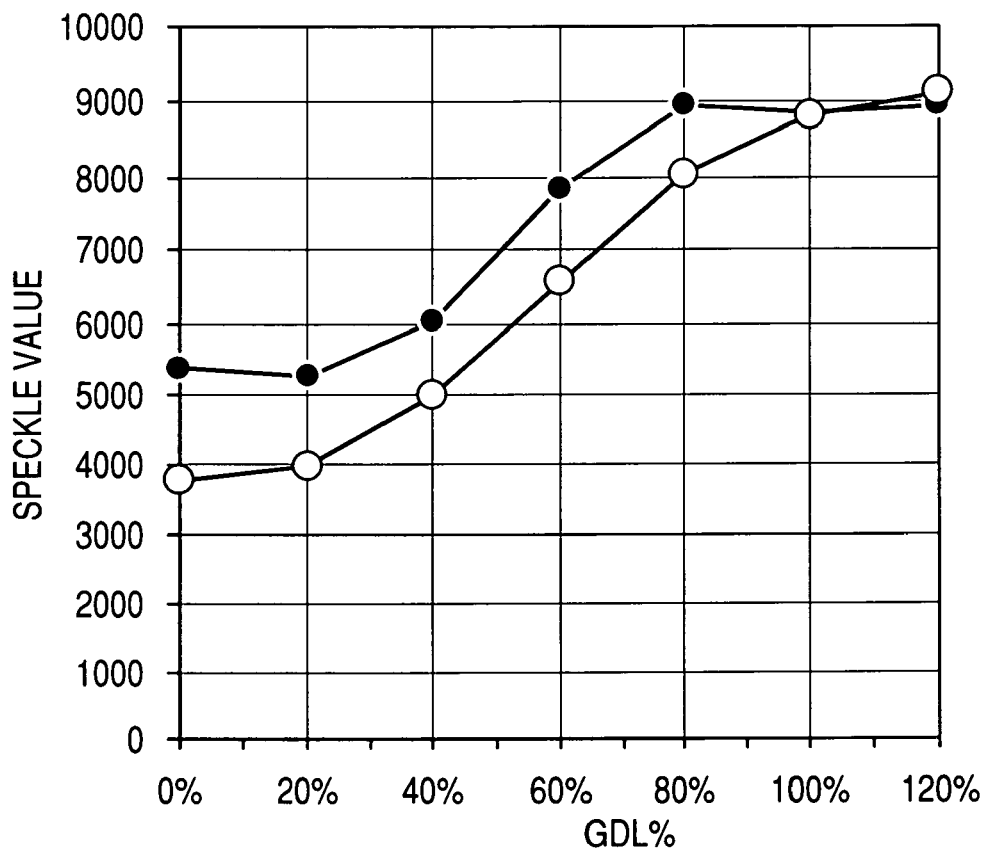
FIG. 19 is an explanatory drawing on the relationship between hardness of a packed tofu and speckle value (observed value) under an excitation condition, described in claim 6 and Example 6 of the invention.

Speckle value (cubic differentiation average value) of packed tofu prepared in the same manner as in the aforementioned Example 2 by adding varied amount of GDL to a soybean milk of 11.5% brix was measured under static condition and excitation condition (excitation at 19 kHz and 2 W/cm$^2$ by installing a commercially available ultrasonic oscillator on pad), and its relationship with fracture force was examined, with the results shown in FIG. 19. A high correlation with hardness was obtained under the excitation condition rather than the completely static condition.

Example 7

Figure 15:
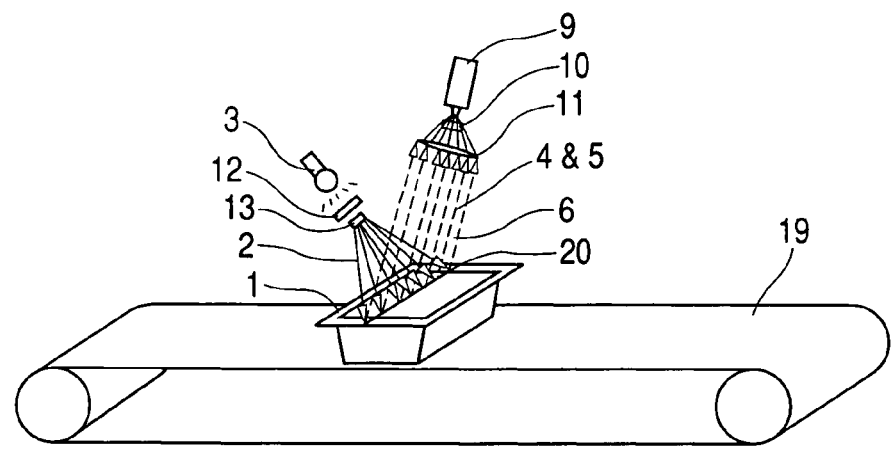
FIG. 15 is an explanatory drawing on an embodiment of the device (linear light source) described in claim 7 and Example 7 of the invention.
Figure 18:
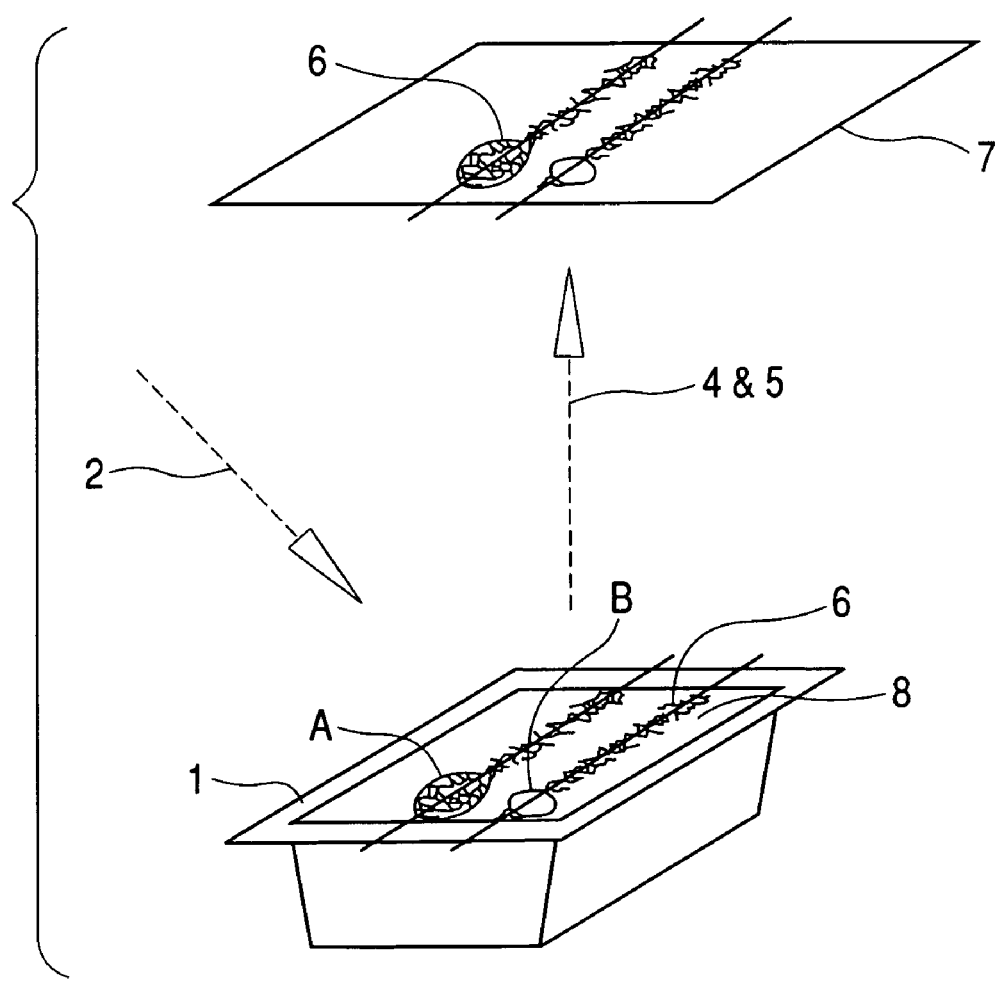
FIG. 18 is an explanatory drawing on the detection of a heterogeneous part of a material body, described in claim 7 and Example 7 of the invention.

As shown in FIG. 15, the linear light 2 was irradiated from the laser beam source 3, traversing the traveling direction of the aforementioned material body 1, in the state in which the aforementioned material body 1 was continuously moving on the conveyer 19, and while the aforementioned material body I was traveling, the lights 4 and 5 reflecting from the image formation 20 of the linear irradiation light and the light 6 of speckle pattern were continuously measured using the aforementioned two-dimensional observation device 9. As a result, distribution of speckle values was obtained on the full face of image formation face. Based on this, it was able to detect a product in which a hard moiety shown by an arrow A in FIG. 18 and a soft moiety shown by an arrow B are present on its surface and inner part.

Figure 16:
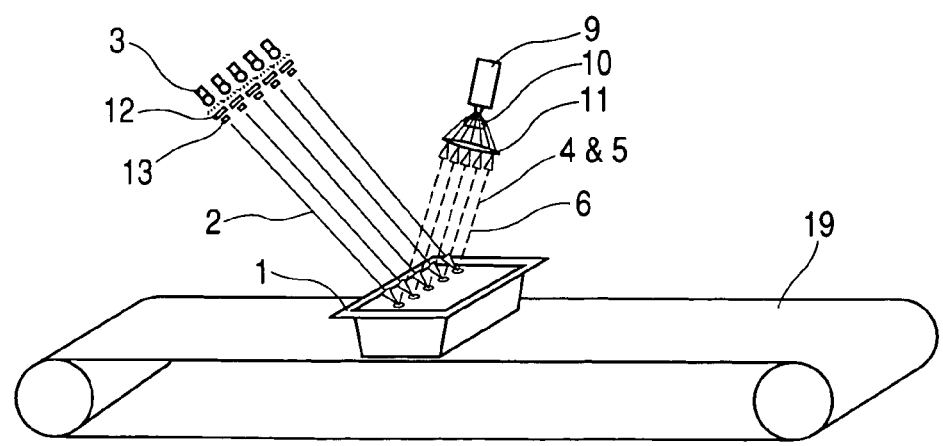
FIG. 16 is an explanatory drawing on an embodiment of the device (transverse line arrangement of spot light source) described in claim 7 and Example 7 of the invention.
Figure 17:
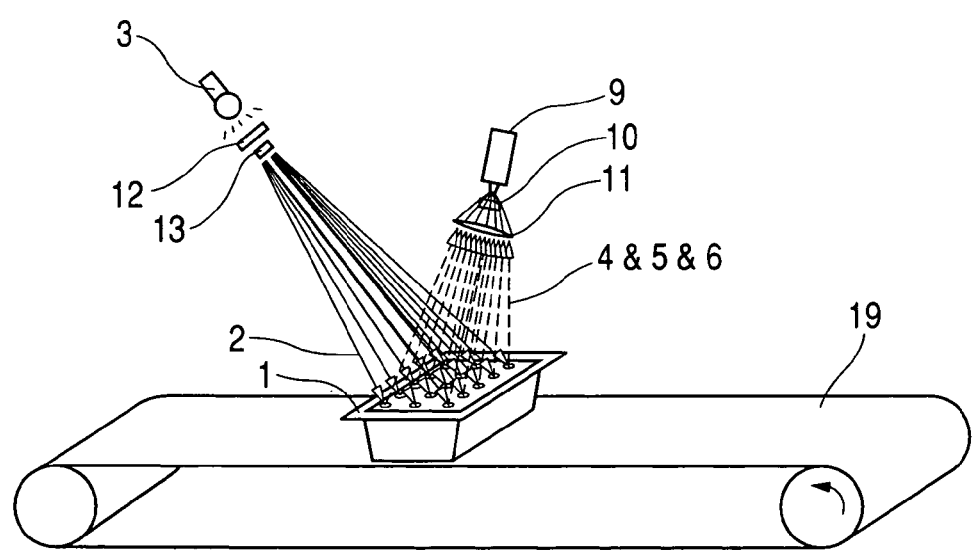
FIG. 17 is an explanatory drawing on an embodiment of the device (two-dimensional arrangement of spot light source) described in claim 7 and Example 7 of the invention.

In addition to this, speckle values can be obtained on the almost full face of image formation face by an embodiment in which spot lights are arranged sideways like the case of FIG. 16 and another embodiment in which spot lights are two-dimensionally arranged (at the time of intermittent moving) like the case of FIG. 17.

While the invention has been describe in detail and with reference to specific embodiments thereof, it will be apparent to one skilled in the art that various changes and modifications can be made therein without departing from the spirit and scope of the invention.

This application is based on a Japanese patent application filed on Mar. 28, 2002 (Japanese Patent Application No. 2002-092979), the entire contents thereof being thereby incorporated by reference.

INDUSTRIAL APPLICABILITY

According to the method of the invention for evaluating a gel state or a sol-gel state change of a material body, which is characterized in that the aforementioned material body is a gel shape material body (or food) or a gel-formable sol shape material body (or food), and said material body illuminated by a coherent light-illuminating light illumination device is evaluated using a two dimensional image observation system equipped with a two dimensionally detecting image recognizing means to observe an image formation of a light beam section or a speckle pattern formed on the image formation face, as described in claim 1 and claim 3, semi-coagulated, un-coagulated and the like defective articles can be distinguished without exception by realizing objective judgment, non-destructive measurement, non-contact measurement, quick measurement and 100% inspection on the change of gel shape material bodies or food to gelled states (hardness and the like) or sol shapes, or the change of gel-formable sol shape material bodies or food to gelled states. As a result, since defective articles are not shipped, occurrence of claims, compensation problems and the like troubles can be prevented. In addition, since this becomes a useful index for the production process control, quality control can be precisely carried out so that it becomes possible to confine futile loss to the minimum.

In case that at least a part of the intervening member is light-transmittable as described in claim 2 of the invention, the aforementioned material body is applicable even when it is a packaged product or in a tank or piping equipped with an inspection window, so that it is not necessary to unseal it or to collect the contents directly, and a burden on the quality control and product loss can therefore be reduced.

By selecting wavelength of irradiation light (e.g., from visible light to near infrared) as described in claim 4 of the invention, influences of the packaging material of packaged products, printing, outdoor light (stray light) and water or the like solvent can be prevented to the minimum so that information on not only the surface but also inner tissue can be obtained.

As described in claim 5 of the invention, among the aforementioned packaged products, a defective product in which water is penetrated into its inner part due to a pin hole or improper sealing and a product in which released water is present, due to the presence of a step for contacting with water, can also be detected so that a burden to the product inspection work can be reduced.

By allowing a product and an observation device to move in a relative manner as described in claim 6 of the invention, full face of the inspection face of a product or almost full face thereof can become the object, and products having partial abnormalities can also be detected without exception. In addition, quick and 100% inspection also becomes easy.

The invention claimed is:

1. A method for evaluating a material body by a scattered light observation system which observes a gel state or a gel-formable sol state material body illuminated with a coherent light through a two dimensional image recognizing means, comprising measuring a gel state or a change in sol-gel state of said material body using a light section formed on an image forming surface or conditions of a speckle pattern.

2. The method for evaluating a material body according to claim 1, wherein the material body is a gel shape food article or a gel-formable sol shape food article, and its quality and change in quality are evaluated.

3. The method for evaluating a material body according to claim 1, wherein a member having at least a part through which irradiated light can permeate is intervened between the material body and the two-dimensional image recognizing means.

4. The method for evaluating a material body according to claim 1, wherein wavelength of irradiation light is within the range of from visible light to near infrared.

5. The method for evaluating a material body according to claim 2, wherein a released state of water existing in a sealed and packaged product of the material body is detected.

6. The method for evaluating a material body according to claim 1, wherein the material body is put in a dynamic state.

7. A measuring system, comprising:
   a coherent light source for emitting a coherent light onto a material; and
   an image recognizing device structured and arranged to measure a gel state or change in sol-gel state of the material by receiving a speckle pattern of the coherent light from the material.

8. The measuring system of claim 7, wherein the coherent light source comprises one of: a laser, a mercury arc lamp, a white light source, an incandescent light, a sodium lamp, an infrared light source, and an ultraviolet light.

9. The measuring system of claim 7, wherein the coherent light is in the shape of a line or an assembly of points.

10. The measuring system of claim 7, wherein the image recognizing device comprises one of: a CCD camera, a MOS camera, a TV camera, a video camera, an image tube, an image intensifier, and a digital camera.

11. The measuring system of claim 7, further comprising a predetermined relational expression of speckle values and gel state or change in sol-gel state values.

12. The measuring system of claim 7, further comprising:
   a container that holds the material; and
   an inspection hole disposed in the container,
   wherein the coherent light is emitted into the inspection hole.

13. The measuring system of claim 12, further comprising a vibrator that shakes the material in the container.

14. The measuring system of claim 12, wherein the container comprises a pipe.

15. The measuring system of claim 7, further comprising:
   a first optical fiber connected to the coherent light source; and
   a second optical fiber connected to the image recognizing device.

16. The measuring system of claim 7, further comprising a moving device that moves the material past the coherent light source and the image recognizing device.

17. The measuring system of claim 7, further comprising:
   a first lens disposed between the coherent light source and the material; and
   a second lens disposed between the image recognizing device and the material.

18. The measuring system of claim 7, wherein the material comprises one of: agar gel, gelatin gel, tofu, konnyaku jelly, collagen gel, silicone gel, silica gel, resin, natural rubber, synthetic rubber, lacquer, paint, milk, soybean milk, bean curd, custard, pudding, and raw egg liquid.

* * * * *